US006808515B2

(12) United States Patent
Takahashi et al.

(10) Patent No.: US 6,808,515 B2
(45) Date of Patent: Oct. 26, 2004

(54) MULTIPLE CONTINUOUS TYPE LIQUID WASTE DISPOSAL APPARATUS

(75) Inventors: Masao Takahashi, Gunma-ken (JP); Kazuo Koike, Tokyo (JP); Eiichi Takano, Tokyo (JP)

(73) Assignees: Gunma Koike Co., Ltd., Gunma-ken (JP); Koike Medical Co., Ltd., Tokyo (JP)

(*) Notice: Subject to any disclaimer, the term of this patent is extended or adjusted under 35 U.S.C. 154(b) by 0 days.

(21) Appl. No.: 09/882,252

(22) Filed: Jun. 18, 2001

(65) Prior Publication Data

US 2002/0026160 A1 Feb. 28, 2002

(30) Foreign Application Priority Data

Jun. 19, 2000 (JP) .................................. 2000-182728

(51) Int. Cl.[7] .............................. A61M 1/00; B67C 3/00; F17D 1/00
(52) U.S. Cl. ........................... 604/320; 141/35; 137/571
(58) Field of Search ............................. 604/319–326, 604/317; 141/35, 36; 137/571; 255/263, 265

(56) References Cited

U.S. PATENT DOCUMENTS

| 3,757,783 | A | * | 9/1973 | Alley ......................... 604/321 |
| 3,938,540 | A | * | 2/1976 | Holbrook et al. ........... 137/205 |
| 4,384,580 | A | * | 5/1983 | Leviton ....................... 604/119 |
| 4,388,922 | A |   | 6/1983 | Telang |
| 5,185,007 | A | * | 2/1993 | Middaugh et al. ............ 141/65 |
| 5,470,324 | A | * | 11/1995 | Cook et al. .................. 600/573 |
| 6,056,731 | A | * | 5/2000 | Koetke et al. ............... 604/317 |
| 6,152,902 | A | * | 11/2000 | Christian et al. ........... 604/319 |

FOREIGN PATENT DOCUMENTS

EP 0394687 10/1990

OTHER PUBLICATIONS

Patent Abstracts of Japan, vol. 1997, No. 07, Jul. 31, 1997.
Patent Abstracts of Japan, JP2000079162, Mar. 21, 2000.
Patent Abstracts of Japan, JP2001190607, Jul. 17, 2000.

* cited by examiner

Primary Examiner—John J. Calvert
Assistant Examiner—C Lynne Anderson
(74) Attorney, Agent, or Firm—Townsend & Banta

(57) ABSTRACT

The object of this invention is to provide a multiply connected type liquid waste disposal apparatus to unify the kind of canister bottles used for multiple connection, to provide plural patient hoses for separate use, to enable easy visual recognition of a content capacity even if a liquid waste disposing capacity is increased, and to rapidly solidify an absorbed liquid waste.

Plural canister bottles forming a straight line by being serially connected in order, wherein:

the patient hose 14 is connected to the absorption port of the lying member L1; the discharge port 8 of lying member L1 and the absorption port 7 of the lying member L2, the discharge port 8 of lying member L2 and the absorption port 7 of the lying member L3, and the discharge port 8 of lying member L3 and the absorption port of the lying member L4 are respectively serially connected with the connection pipe 15; the connection pipe 15 connected to the discharge port 8 of the lying member L4 arranged at the terminal row is connected to the closing stopper 16 of the lid 3; and the absorption pressure is applied from the exhaust port 9 of each lying member L. Each lying member L contains the float 5 retaining the solidifying agent 6 and the stop valve 9a serves to cease the absorption pressure from the exhaust port 9 when the float 5 floats inside the liquid waste 21 and reaches the ceiling portion.

7 Claims, 16 Drawing Sheets

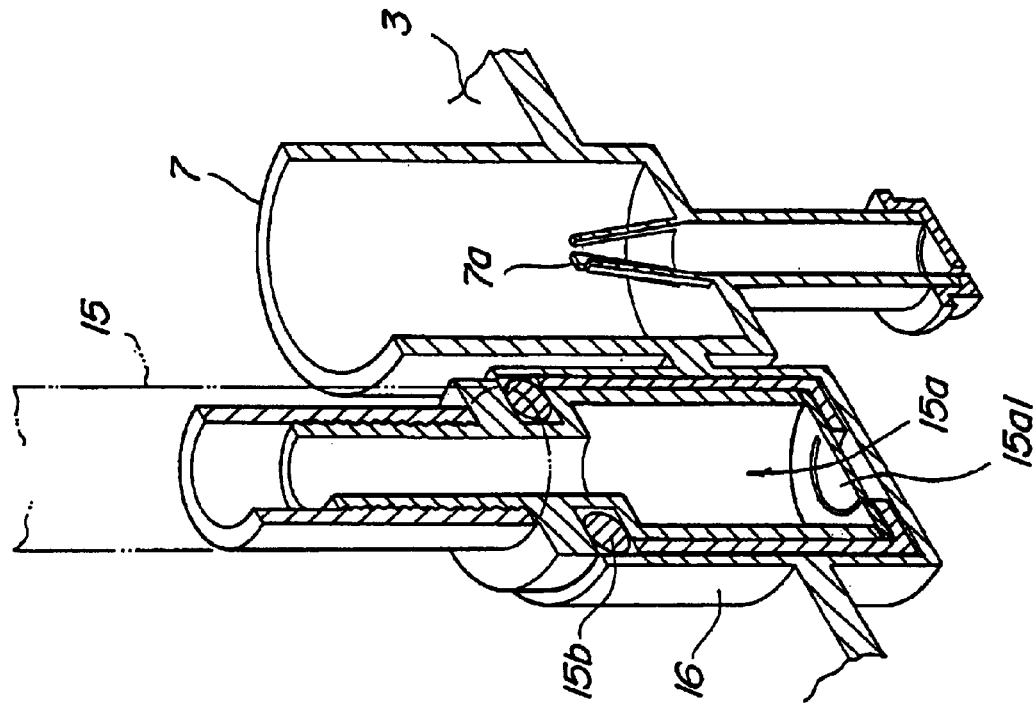
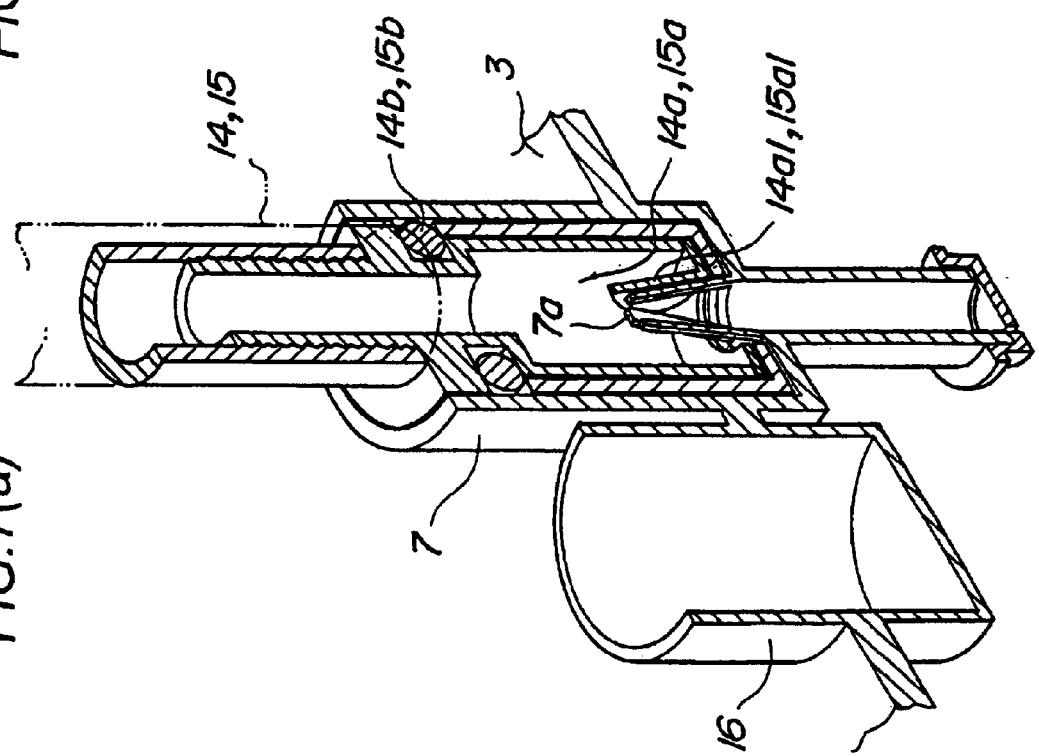
FIG. 7(a)
FIG. 7(b)

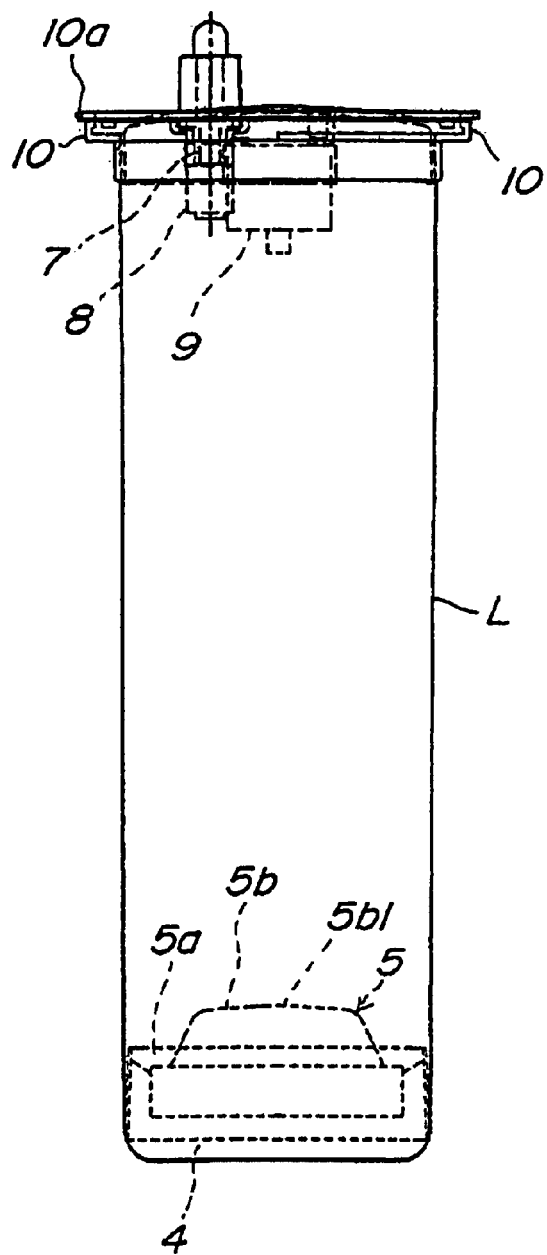
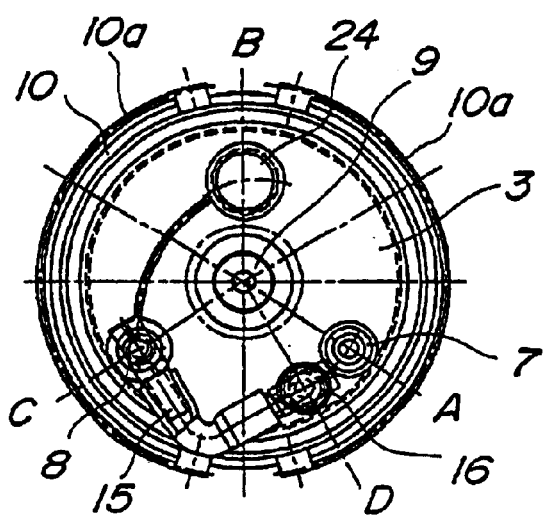
FIG.8(a)
FIG.8(b)

FIG.9(a)
FIG.9(b)
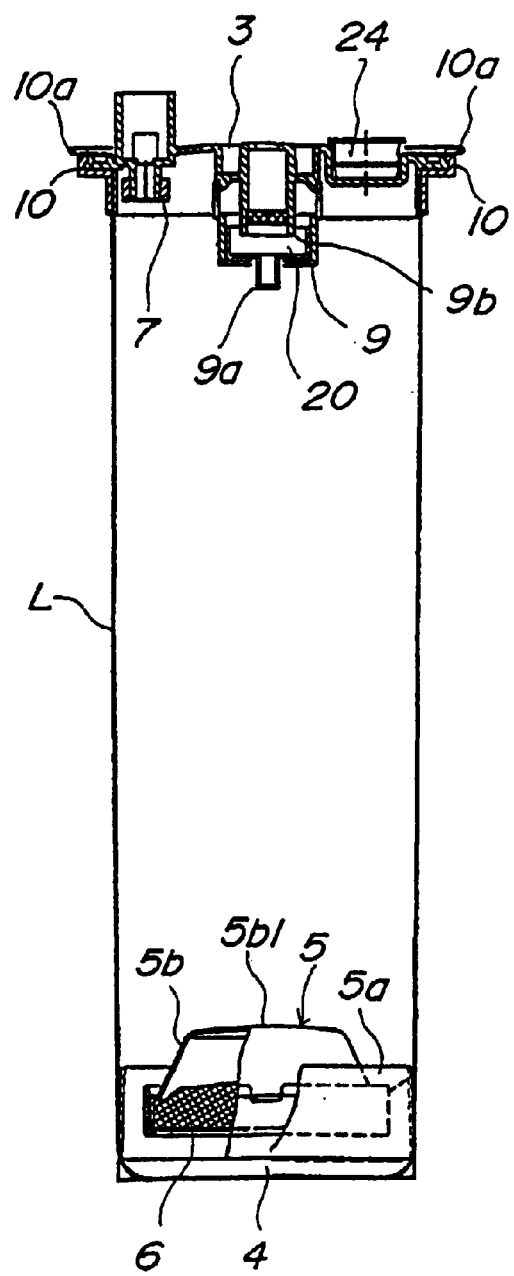
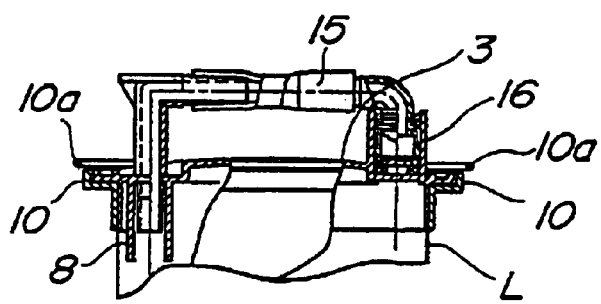

MULTIPLE CONTINUOUS TYPE LIQUID WASTE DISPOSAL APPARATUS

CROSS-REFERENCE TO RELATED APPLICATION

The entire disclosure of Japanese patent application No. 2000-182728 filed on Jun. 19, 2000, including the specification, claims, accompanying drawings and abstract of the disclosure is incorporated herein by reference in its entirety, in order to claim priority right according to 35 U.S.C. §119.

BACKGROUND OF THE INVENTION

1. Field of the Invention

This invention relates to a liquid waste disposal apparatus serving to absorb, to solidify and to dispose a liquid waste such as unwanted blood, other body fluids, secretion derived from a medical scene or pus or physiological sodium chloride solution used for cleansing affected areas.

2. Description of Related Art

A liquid waste (e.g. unwanted blood, other body fluids, secretion, pus, or physiological sodium chloride solution used for cleansing affected areas) derived from medical scenes, particularly at a scene of surgical operation, is collected into a container or a collecting bag for disposal and incineration by an absorbing apparatus.

However, since the liquid waste may contain a harmful bacteria or the like, a secondary infection may occur among medical employees, hospital patients and the like, when the container or the collecting bag becomes damaged or when an excessive amount of the liquid waste is absorbed exceeding a capacity of the collecting bag.

For preventing thus created problem, an apparatus for solidifying a liquid waste with a water-absorptive material arranged inside a collecting bag is provided and methods for arranging the liquid waste solidifying water-absorptive material inside the collecting bag are provided such as: a method of forming a collecting bag with a non-water permeable sheet and a water-absorptive sheet stuck with each other in which the water-absorptive sheet is arranged as an inner surface, a method of dropping a prepared water-absorptive material into a collecting bag after an absorption of liquid waste, or a method of fixing a water-absorptive material at a bottom portion of a collecting bag.

Furthermore, in means to increase the liquid waste disposing capacity of a liquid waste disposal apparatus, a liquid waste disposal apparatus having 2 continuously arranged collecting bags, or a liquid waste disposal apparatus having 4 or 6 consecutively arranged collecting bags disposed along a same circumference on top of a wheeled base are being proposed, and further, a shutting off valve or the like could be provided at the terminal row of the collecting bags for automatically stopping an absorption of the liquid waste when multiple collecting bags are serially connected to form a straight line.

Nevertheless, when the multiple collecting bags are connected along a same circumference for increasing the liquid waste disposing capacity, a user of the disposing apparatus could not easily confirm the remaining containment capacity of the disposing apparatus since the collecting bags were unable to be viewed from a single direction.

Further, when the multiple collecting bags are connected forming a straight line, a special kind of collecting bag differentiated from the rest of the collecting bags is required for a collecting bag arranged at the terminal row since the collecting bag arranged at the terminal row is requires the shutting off valve; accordingly, thus requiring of a different kind of collecting bag raises a problem of increasing production costs and increasing product management costs.

Further, the disposal apparatus structured with the non-water permeable sheet and the water-absorptive sheet stuck with each other caused an inner portion to be unable to be seen from outside and also caused difficulty of folding and also caused inconvenience during storage and transport owing to a multiple overlapping structure of the disposal apparatus.

Further, the disposal apparatus using the method of dropping a prepared water-absorptive material into a collecting bag after the absorption of liquid waste is unable to perform further absorption once a solidification process is completed and also a danger remained when toppled during the middle of an operating process since solidification would not proceed until the water-absorptive material is dropped inside the collecting bag.

A disposal apparatus using the method of fixing a water-absorptive material at a bottom portion of a collecting bag would cause a solidifying speed to decrease in association with the proceeding of the liquid waste absorption process.

SUMMARY OF THE INVENTION

This invention is aimed to solve the foregoing problems, and an object thereof resides in providing a multiply connected type liquid waste disposal apparatus to unify the kind of canister bottles used for multiple connection, to provide plural patient hoses for separate use, to enable easy visual recognition of a containment capacity even if a liquid waste disposing capacity is increased, and to solidify more rapidly an absorbed liquid waste.

The multiple continuous type liquid waste disposal apparatus regarding this invention comprises: n (n being equal to or more than 3)connected canister bottles; the canister bottles having an absorption port and a discharge port; the canister bottles containing a liquid waste absorbed from the absorption port; the canister bottles enabling the contained liquid waste to be seen from outside, wherein: the discharge port of a first canister bottle is connected to the absorption port of a second canister bottle, and the discharge port of the second canister bottle is connected to the absorption port of a third canister bottle, and . . . the discharge port of n−1 canister bottle is connected to the absorption port of n canister bottle; and the foregoing canister bottles form a straight line by being serially connected in an order starting from the first canister bottle to the n canister bottle.

Thus structured, this invention enables all of the canister bottles to be viewed from a single direction by serially connecting the canister bottles in an order starting from the first canister bottle to the n (n being equal to or more than 3)canister bottle and forming a straight line; this invention also allows the user of the disposal apparatus to easily confirm the remaining containment capacity of the disposal apparatus since the liquid waste is contained in an order starting from the first canister bottle to the n canister bottle.

The multiple continuous type liquid waste disposal apparatus regarding this invention is further structured with plural connected canister bottles, each of the canister bottles having an absorption port for absorbing liquid waste, each of the canister bottles having a discharge port for discharging liquid waste, each canister bottle serving to contain the liquid waste absorbed from the absorption port; wherein, each of the canister bottles has an exhaust port for creating negative pressure inside the canister bottle; the discharge port of one canister bottle is connected to the absorption port of the other canister bottle in a serially connected manner; and the exhaust port of a terminally arranged canister bottle is closed.

Thus structured, this invention enables the liquid waste to be absorbed and contained consecutively into the serially connected multiple canister bottles by connecting the discharge port of one canister bottle to the absorption port of another canister bottle and forming a serial connection while closing the discharge port of the canister bottle arranged at the terminal row to allow exhaustion from the exhaust port of each canister bottle for internally creating negative pressure.

This invention could also reduce the kind of canister bottle to allow the reduction of production cost and product management cost since the kind of canister bottle used for the canister bottle arranged at the terminal row is unified with that of the other canister bottles.

This invention also enables all of the canister bottles to be viewed from a single direction by serially connecting the plural canister bottles in order so as to form a straight line; this invention also allows the user of the disposal apparatus to easily confirm the remaining containment capacity of the disposal apparatus since the liquid waste is contained in the order according to the arrangement of the canister bottles.

The multiple continuous type liquid waste disposal apparatus regarding this invention is further structured with plural connected canister bottles, each of the canister bottles having an absorption port for absorbing liquid waste, each of the canister bottles having a discharge port for discharging liquid waste, each canister bottle serving to contain the liquid waste absorbed from the absorption port; wherein: each of the canister bottles has an exhaust port for creating negative pressure inside the canister bottle; the canister bottles are separated into at least two groups in which the discharge port of one canister bottle is connected to the absorption port of the other canister bottle in a serially connected manner; each of the separated canister bottle groups has a terminal canister bottle with a closed discharge port; and each of the separated canister bottle groups has a primary canister bottle with a patient hose connected to the absorption port.

Thus structured, this invention allows the plural patient hoses for each of the separated canister bottle groups to be used separately and enables the liquid waste to be absorbed and contained consecutively into the serially connected multiple canister bottles by providing the foregoing constitution wherein: each of the canister bottles has an exhaust port for creating negative pressure inside the canister bottle; the canister bottles are separated into at least two groups in which the discharge port of one canister bottle is connected to the absorption port of the other canister bottle in a serially connected manner; each of the separated canister bottle groups has a terminal canister bottle with a closed discharge port; and each of the separated canister bottle groups has a primary canister bottle with a patient hose connected to the absorption port.

This invention could also reduce the kind of canister bottle to allow the reduction of production cost and product management cost since the kind of canister bottle used for the canister bottle arranged at the terminal row of the respective separated canister bottle group is unified with that of the other canister bottles.

This invention also enables all of the canister bottles to be viewed from a single direction by serially connecting the plural canister bottles regarding each group of canister bottles in an orderly manner so as to form a straight line; this invention also allows the user of the disposal apparatus to easily confirm the remaining containment capacity of the disposal apparatus since the liquid waste is contained in the order according to the arrangement of the canister bottles regarding each group of canister bottles.

By providing the canister bottle comprised of an outer container having inside an internal bag containing a solidifying agent, the liquid waste could be solidified inside the internal bag so that the internal bag could be solely and sanitarily disposed.

By providing a float inside the internal bag of the canister bottle in which the float retains the solidifying agent and has a specific gravity less than 1, a liquid level could be easily confirmed from outside by checking the position of the float since the float would always remain afloat at a gas-liquid interface, and the user could also easily confirm the used amount as well as the remaining containment capacity.

In a process where the liquid waste is absorbed, a water-absorptive material could constantly spread among the newly absorbed liquid waste and swiftly and effectively solidify the liquid waste since the float having a specific gravity less than 1 constantly stays afloat at the liquid-gas interface.

Even when the absorption is started once again after a cease of the absorption process, solidification could be performed swiftly, and the float could serve as a level gauge for indicating the amount of content since the float constantly stays afloat at the liquid-gas interface. The manufacturing cost would be inexpensive owing to a simple structure of the float.

BRIEF DESCRIPTION OF THE DRAWINGS

The above and other objects and features of the invention are apparent to those skilled in the art from the following preferred embodiments thereof when considered in conjunction with the accompanied drawings, in which:

FIG. 7 is an explanatory view showing a function of a valve member when a connection tube or a patient hose is connected to a closing stopper and an absorption port arranged at a lid of a ceiling portion of an internal bag;

FIG. 8(a) is an outer front view showing a structure of an internal bag of a canister bottle and a float contained inside the internal bag and serving to retain a solidifying agent within; FIG. 8(b) is an outer plane view showing a structure of an internal bag of a canister bottle;

FIG. 9(a) is a cross-sectional view showing B subtracted by A of FIG. 8(b); FIG. 9(b) is a cross-sectional view showing D subtracted by C of FIG. 8(b);

DETAILED DESCRIPTION OF THE PREFERRED EMBODIMENTS

An embodiment of the multiple continuous type liquid waste disposal apparatus regarding this invention will hereinafter be specifically described with reference to the drawings. FIG. 1 through FIG. 12 are the drawings for explaining a structure of a first embodiment of the multiple continuous type liquid waste disposal apparatus regarding this invention.

Figure 1:
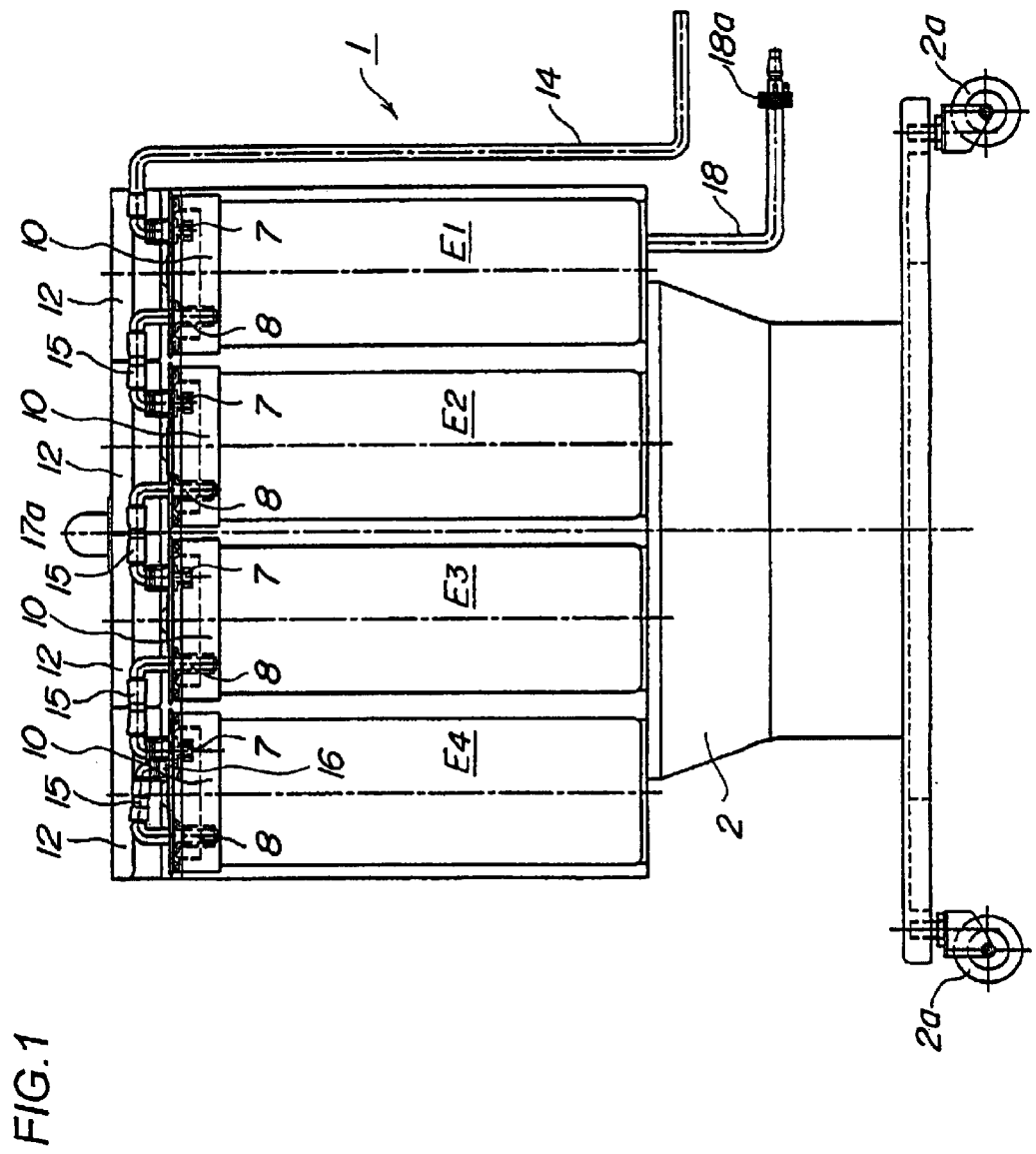
FIG. 1 is an outer front view showing a structure of a first embodiment of a multiple continuous type liquid waste disposal apparatus regarding this invention.
Figure 2:
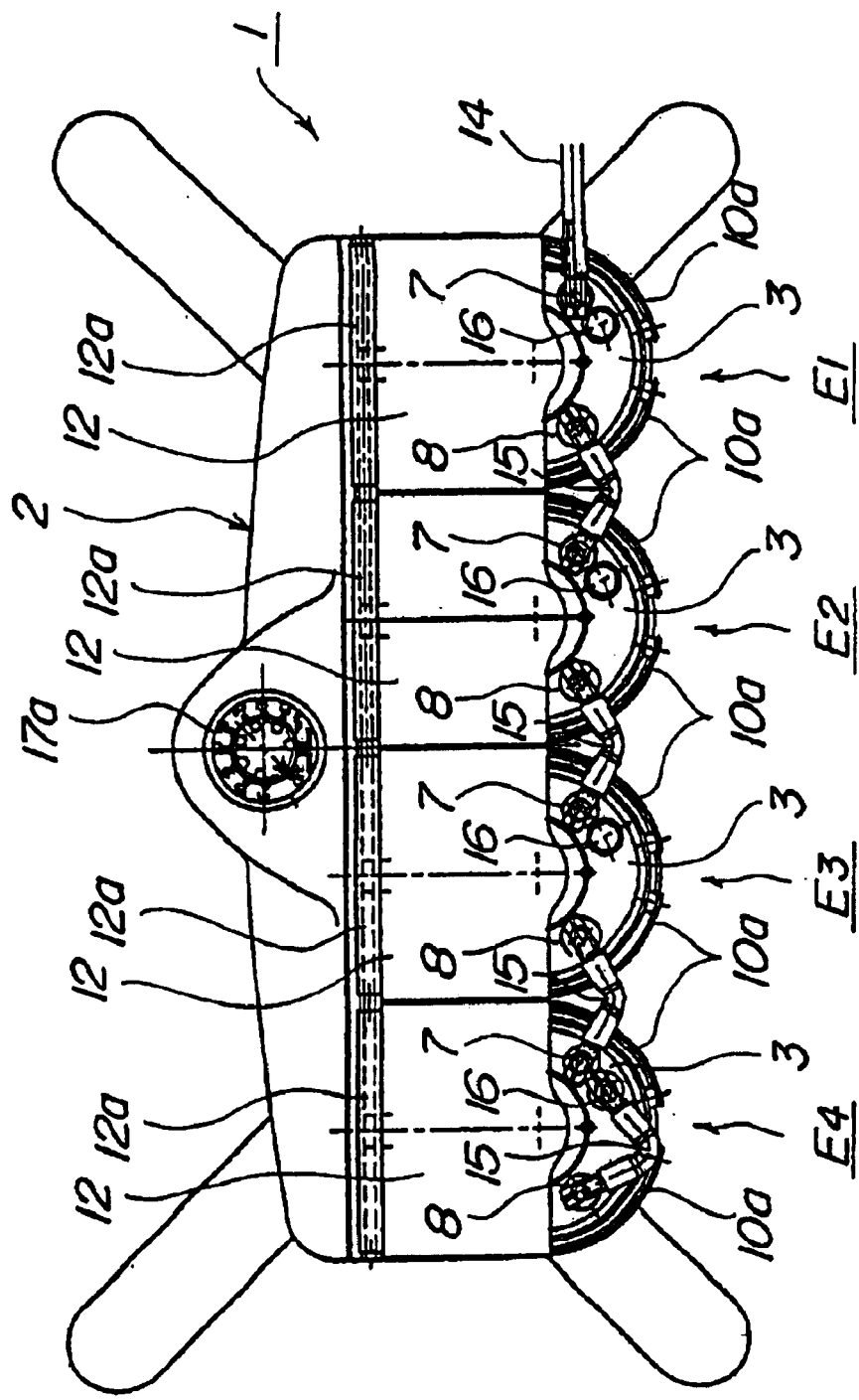
FIG. 2 is an outer plane view showing a structure of the first embodiment of the multiple continuous type liquid waste disposal apparatus regarding this invention.
Figure 3:
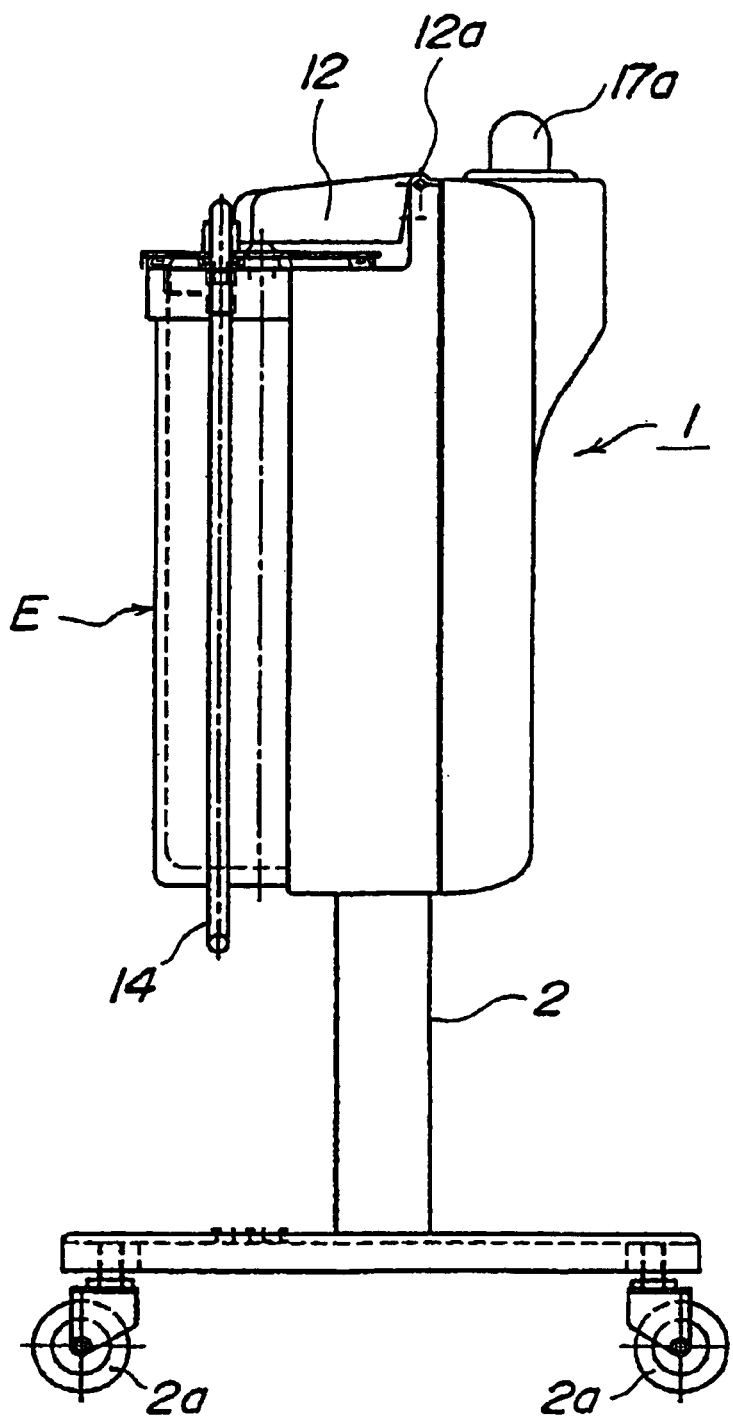
FIG. 3 is an outer side view showing a structure of the multiple continuous type liquid waste disposal apparatus regarding this invention.

FIG. 1 is an outer front view showing a structure of a first embodiment of a multiple continuous type liquid waste disposal apparatus regarding this invention; FIG. 2 is an outer plane view showing a structure of the first embodiment of the multiple continuous type liquid waste disposal apparatus regarding this invention; and FIG. 3 is an outer side view showing a structure of the multiple continuous type liquid waste disposal apparatus regarding this invention.

Figure 4:
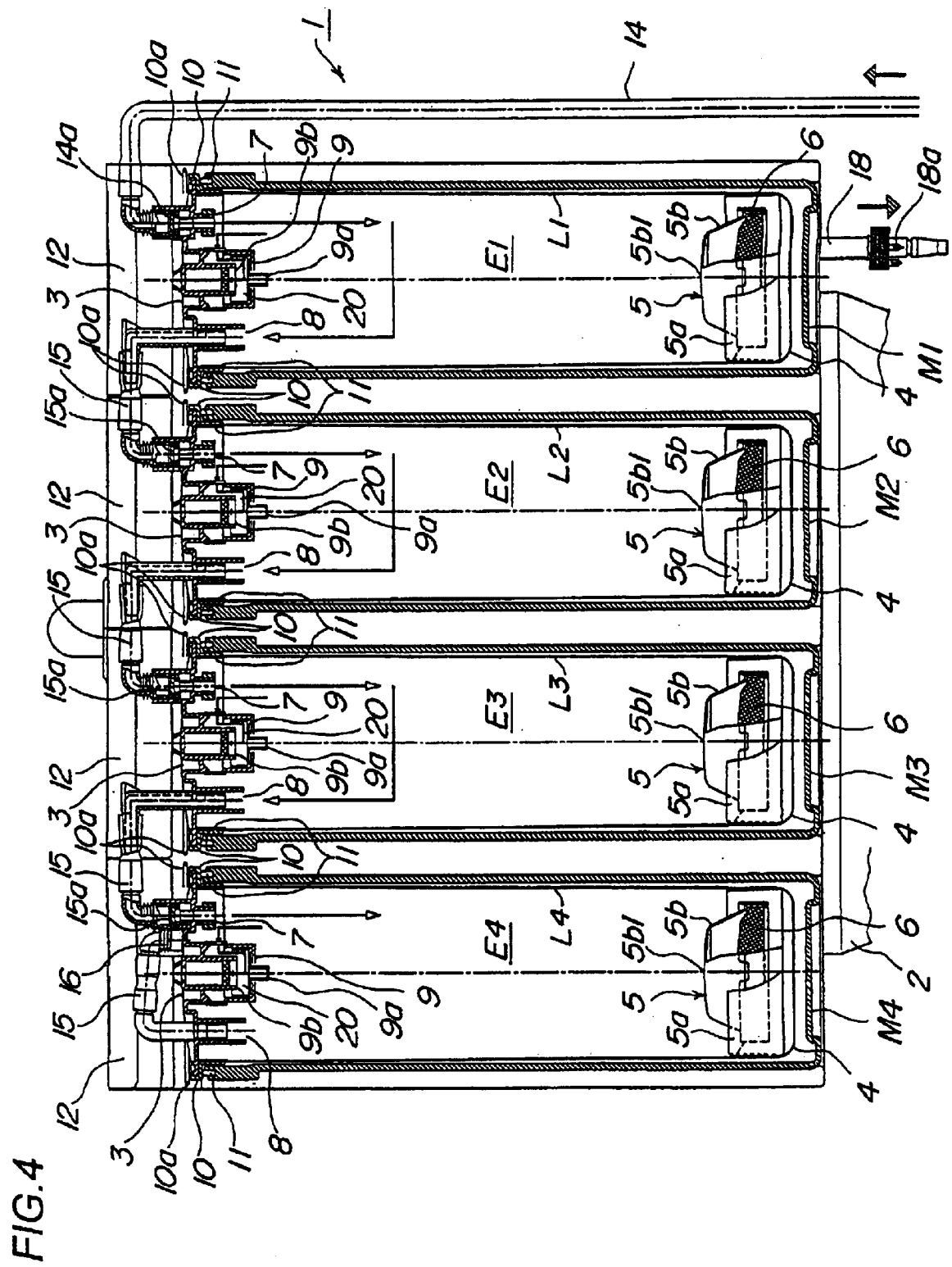
FIG. 4 is a side cross-sectional explanatory view for describing an absorption path of the first embodiment of the multiple continuous type liquid waste disposal apparatus regarding this invention.
Figure 5:
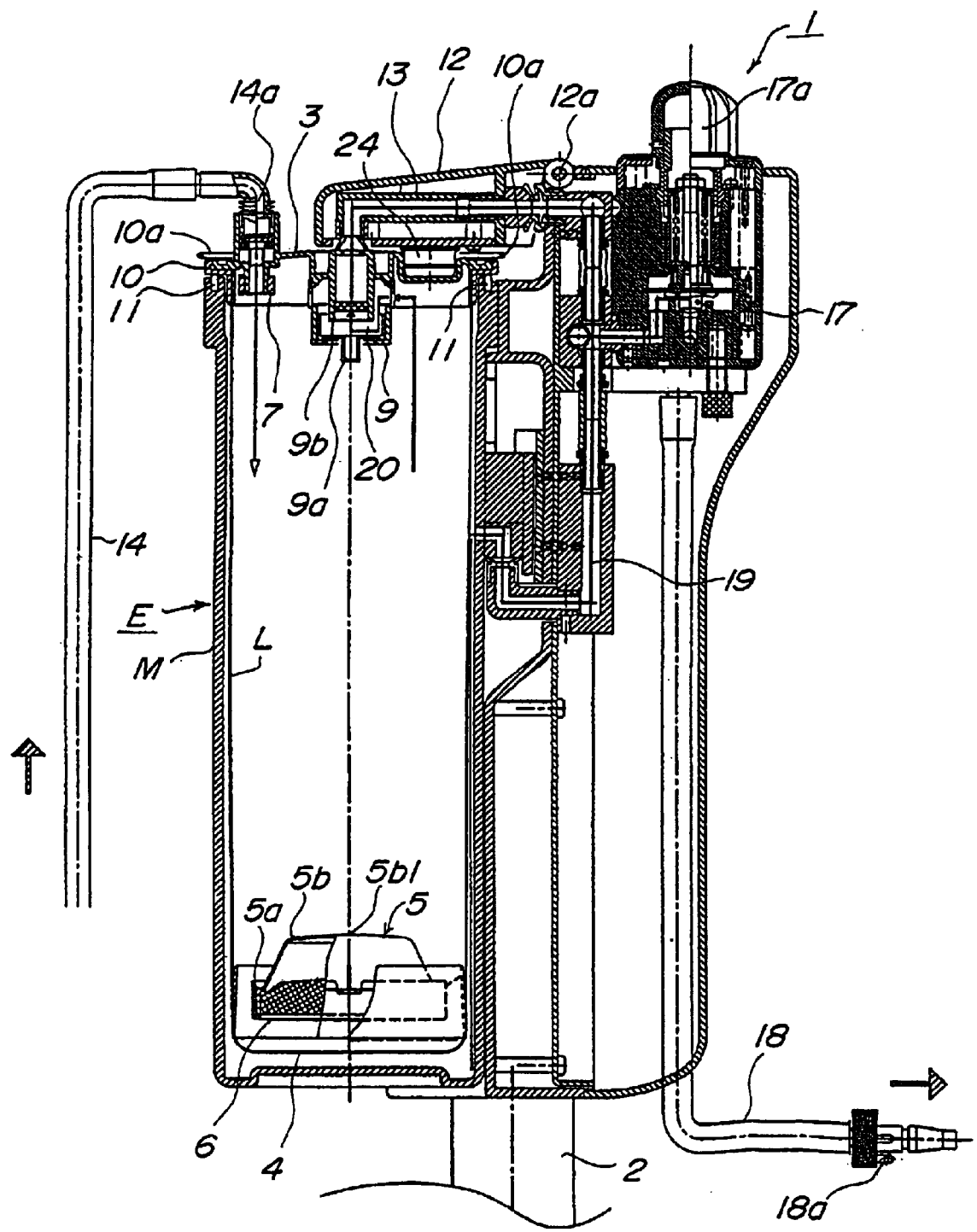
FIG. 5 is a vertical cross-sectional view for describing an absorption path of the multiple continuous type liquid waste disposal apparatus regarding this invention.

FIG. 4 is a side cross-sectional explanatory view for describing an absorption path of the first embodiment of the multiple continuous type liquid waste disposal apparatus regarding this invention; and FIG. 5 is a vertical cross-sectional view for describing an absorption path of the multiple continuous type liquid waste disposal apparatus regarding this invention.

Figure 6:
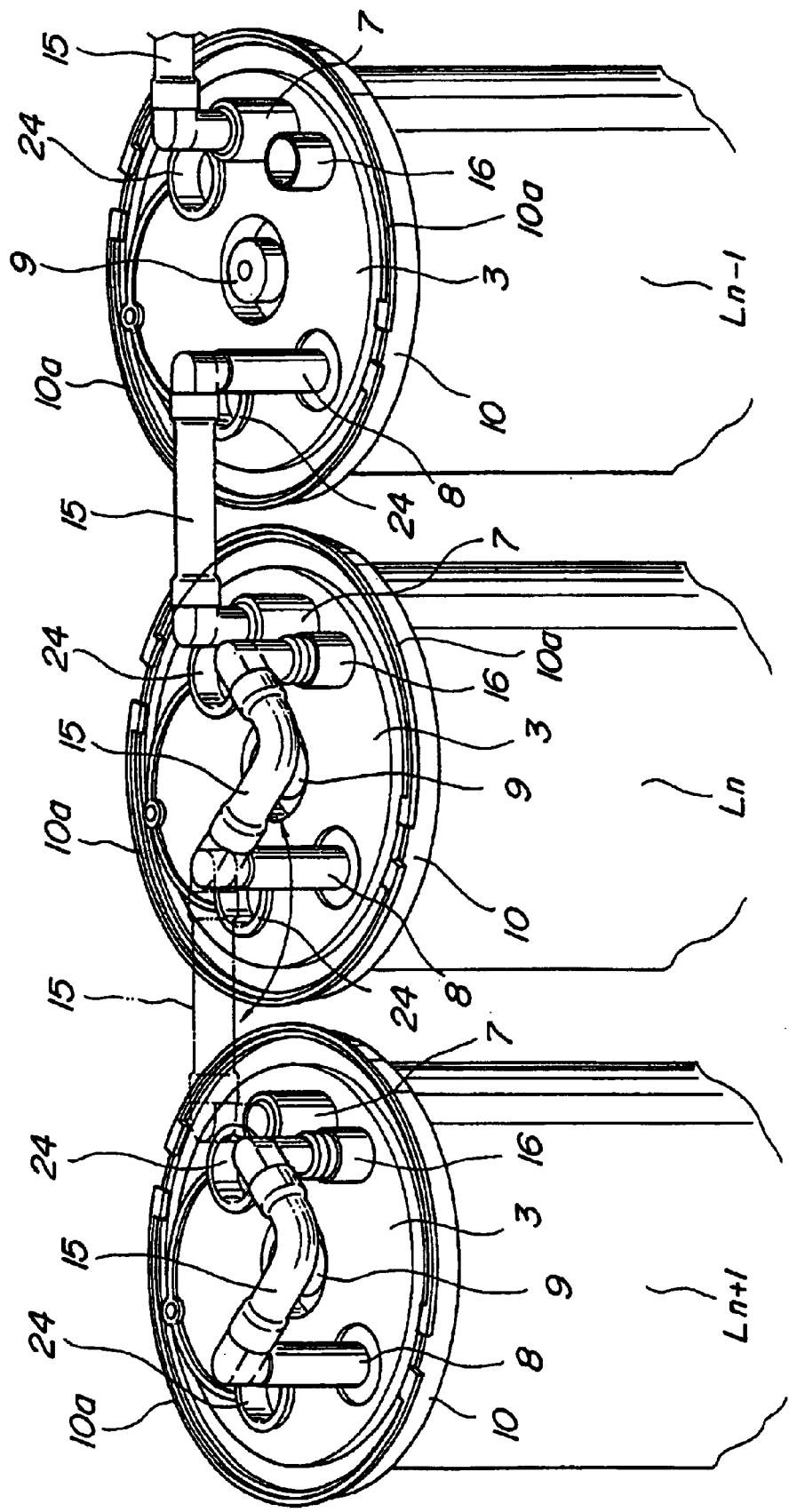
FIG. 6 is a perspective explanatory view showing unified canister bottles in a state where one of the canister bottles could selectively have a closed discharge port when arranged as a terminal canister bottle or could connect to a downstream arranged canister bottle in accordance to circumstance.

FIG. 6 is a perspective explanatory view showing unified canister bottles in a state where one of the canister bottles could selectively have a closed discharge port when arranged as a terminal canister bottle or could connect to a downstream arranged canister bottle in accordance to circumstance; and FIG. 7 is an explanatory view showing a function of a valve member when a connection tube or a patient hose is connected to a closing stopper and an absorption port arranged at a lid of a ceiling portion of an internal bag.

Figure 10:
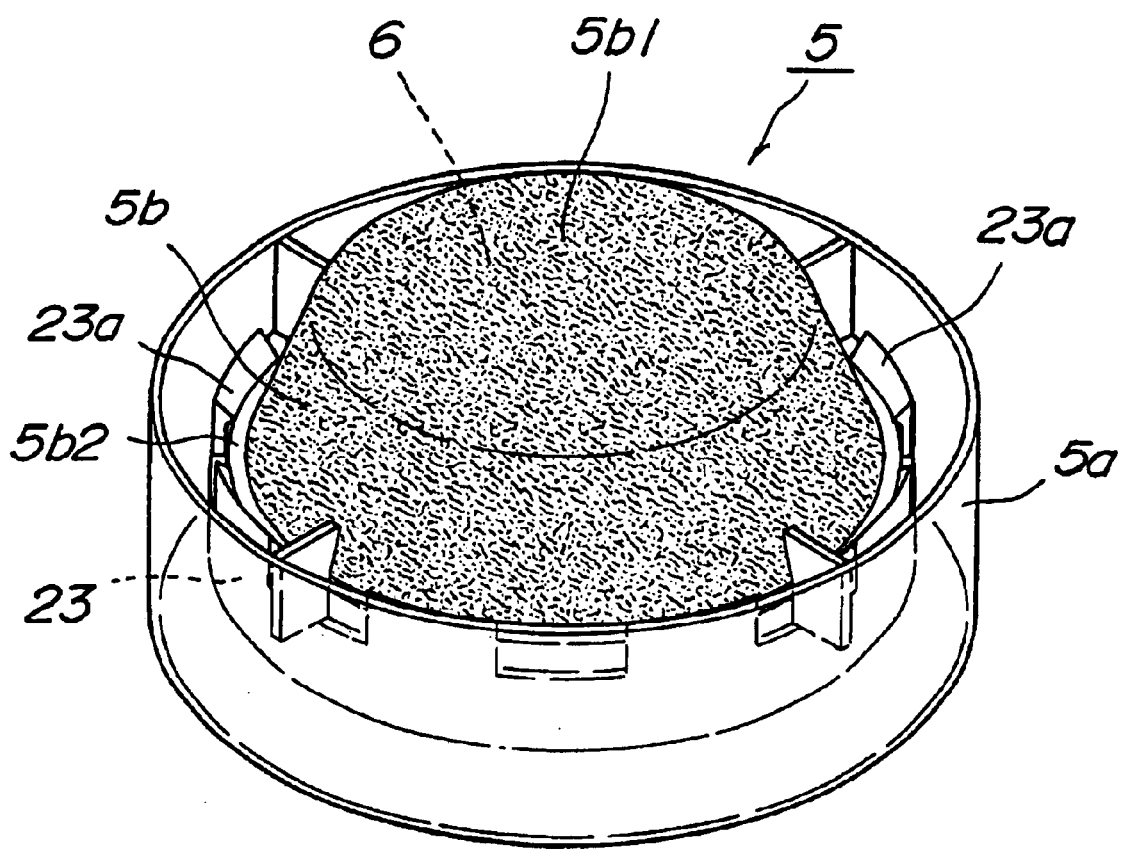
FIG. 10 is a perspective of a structure of a float.
Figure 11:
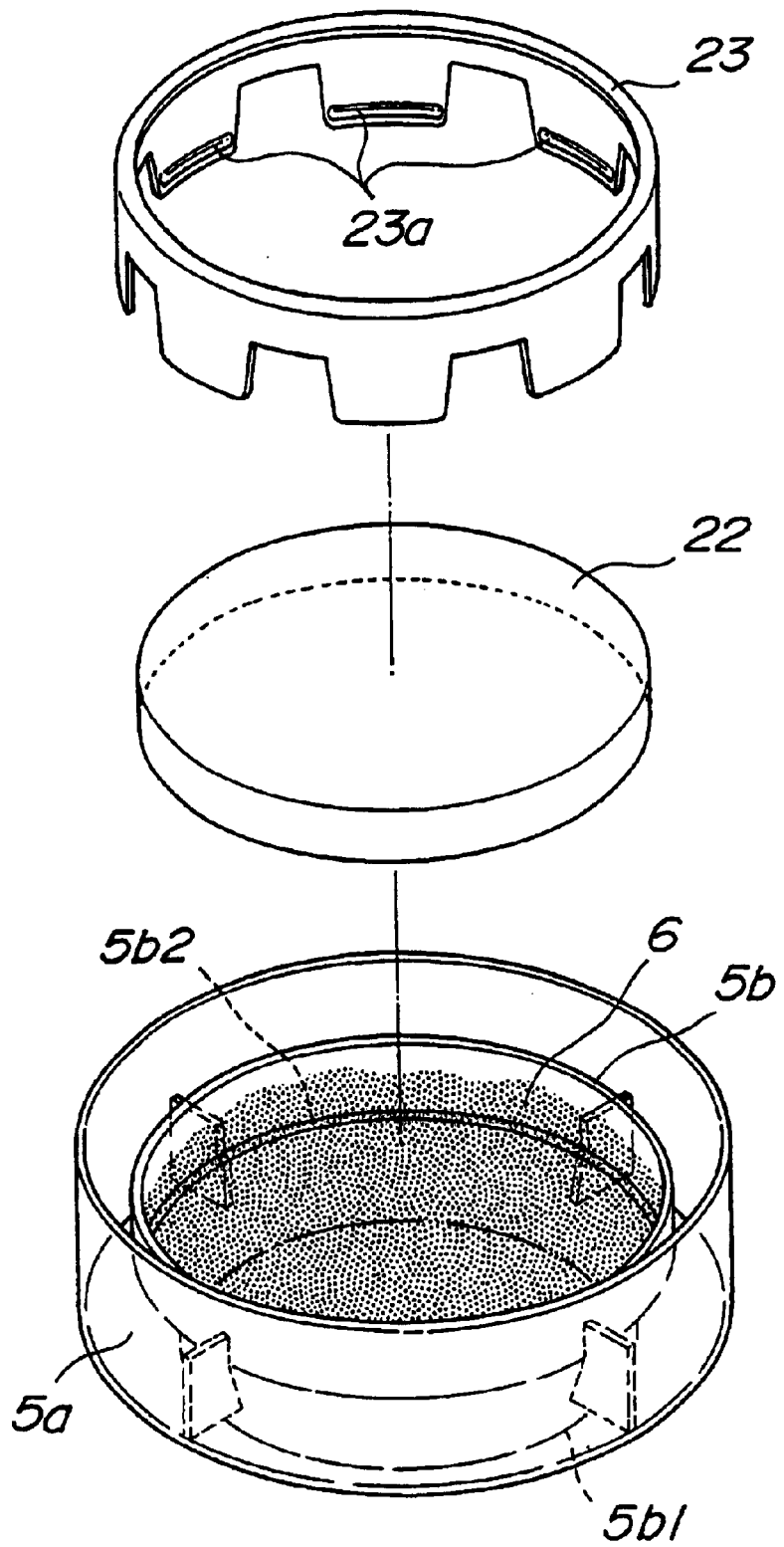
FIG. 11 is an exploded perspective view of a float.
Figure 12:
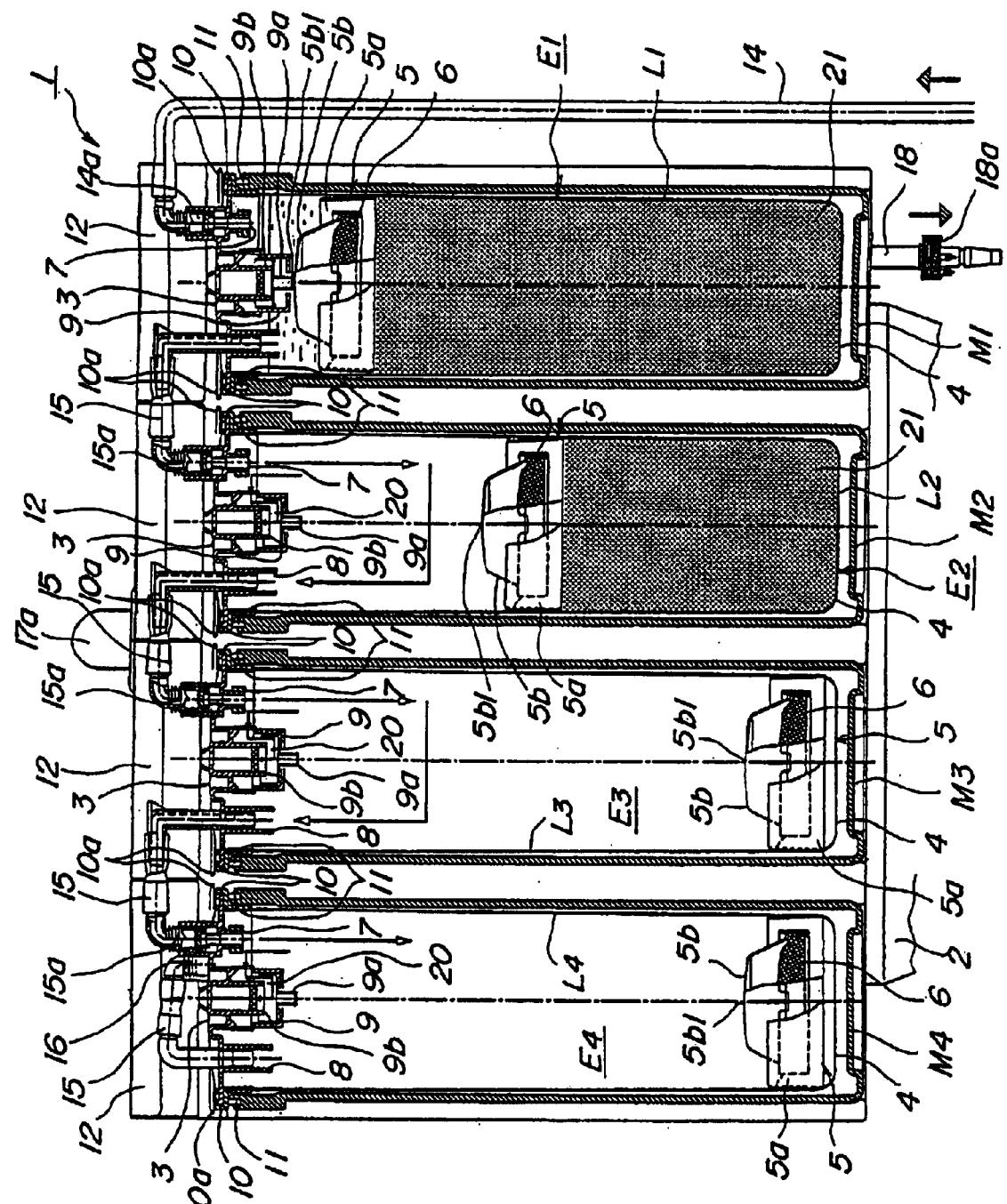
FIG. 12 is a view of a first embodiment of the multiple continuous type liquid waste disposal apparatus regarding this invention showing a state where a liquid waste is absorbed and contained.

FIG. 8(a) is an outer front view showing a structure of an internal bag of a canister bottle and a float contained inside the internal bag and serving to retain a solidifying agent within; FIG. 8(b) is an outer plane view showing a structure of an internal bag of a canister bottle; FIG. 9(a) is a cross-sectional view showing B subtracted by A of FIG. 8(b); FIG. 9(b) is a cross-sectional view showing D subtracted by C of FIG. 8(b); FIG. 10 is a perspective of a structure of a float; FIG. 11 is an exploded perspective view of a float; and FIG. 12 is a view of a first embodiment of the multiple continuous type liquid waste disposal apparatus regarding this invention showing a state where a liquid waste is absorbed and contained.

The embodiment described hereinafter relates to one example of a medical liquid waste disposal apparatus in which a liquid waste 21 (such as dispensable blood, other body fluids, secretion, pus, or physiological sodium chloride solution used for cleansing affected areas produced during operation and treatment) is absorbed into a lying member L serving as an internal bag for a canister bottle E so that the lying member L could be incinerated inclusive of the absorbed liquid waste.

As shown in FIG. 1 through FIG. 5, a multiple continuous type liquid waste disposal apparatus 1 of this embodiment having a canister bottle comprised of a lying member L serving as an internal bag for containing liquid waste 21 and a bottle M serving as an outer container for containing the lying member L in a detachably attached manner, wherein at least 2 or more canister bottles E are connected in series to form a straight line and are supported by a stand 2.

The bottle M shown in FIG. 4 and FIG. 5 is supported by the stand 2 in a detachably attached manner, and a caster 2a is attached to a leg portion of the stand 2. Thus structure allows the stand 2 to steadily move the 2 or more plural canister bottles E in a state where the canister bottles E are supported and arranged in a straight line.

The bottle M is a transparent plastic cylindrical container having an engagement portion arranged at a rear side for detachably engaging with the stand 2 and a graduation formed at a surface for indicating capacity.

The lying member L is a united body having a circular plastic lid 3 thermally welded to an opening portion of a flexible cylindrical transparent bag 4 made from a low density polyethylene. Therefore, the canister bottle E comprised of the bottle M containing the lying member L allows the absorbed and contained liquid waste 21 to be easily visually recognized, and the graduation formed at the surface of the bottle M enables the confirmation of the amount of the liquid waste 21 and the remaining containment capacity.

A floatable float 5 is arranged above a bottom portion 4 inside the lying member L in which the float has a specific gravity less than 1 and retains a water-absorptive material 6 such as a water-absorptive polymer serving as a solidifying agent.

An absorption port 7 and an discharge port 8 arranged at the lid 3 are in liquid-communication to an inside of the lying member L wherein the absorption port 7 absorbs the liquid waste 21 into the lying member L and the discharge port 8 discharges the liquid waste 21 to the absorption port 7 of an adjoining lying member 21.

An exhaust port 9 exhausting air from the lying member 21 for creating a negative pressured state is arranged at a central portion of the lid 3 in an air-communication manner to the inside of the lying member L. Further, a ring-shaped holder 10 having a catch 10a is engaged and fixed to a peripheral portion of the lid 3.

The holder 10 is a united body in which a plastic annular body for engaging and fixing an opening periphery of the bottle M is molded to the catch 10a.

When inserting the lying member L into the bottle M, as shown in FIG. 2, FIG. 3 and FIG. 5, a canister head 12 arranged opposite to the stand 2 and pivotally movable around a pivotal movement shaft 12a as a center would pivotally move and open so that the lying members L1, L2, L3, L4 could respectively be inserted into the four bottles M1, M2, M3, M4 in which the bottles are fixed to the stand 2 and arranged in a straight line.

As shown in FIG. 4 and FIG. 5, when the lying member L is inserted into the bottle M, a cylindrical portion of the holder engaged to an outer peripheral portion of the lid 3 arranged at the ceiling portion of the lying member L is engagedly inserted to the opening portion of the bottle M and thus, a packing 11 arranged at an opening peripheral rim of the bottle M contacts to a collar portion of the holder 10.

When the canister head 12 is closed by pivotally moving the canister head downward around the pivotal movement shaft 12a as the center, as shown in FIG. 5, an absorption path 13 arranged at the canister head 12 is connected in air-communication with the exhaust port 9 arranged at the lid 3 of the lying member L, and at the same time, the lid 3 of the lying member L is fixed to the bottle M via the holder 10 creating an air-tight sealed state at the space between the bottle M and the lying member L via the packing 11 where the lid 3 and the holder 10 are unitedly pressed against the bottle M fixed by the stand 2.

A patient hose 14 is connected to the absorption port 7 arranged at the lid 3 of a first lying member L1 in a state where a first canister bottle E1, a second canister bottle E2, a third canister bottle E3 and a fourth canister bottle E4 are disposed in a straight line and arranged in an order starting from the first lying member L1 to the second canister bottle E2 to the third canister bottle E3 and to the fourth canister bottle E4; the patient hose 14 is applied to a portion such as an affected portion of a patient so as to absorb the liquid waste 21 such as dispensable blood, other body fluids, secretion, pus, or physiological sodium chloride solution used for cleansing affected areas produced during operation and treatment.

The absorption port 7 arranged at the lid 3 of the second lying member L2 is connected to the discharge port 8 arranged at the lid 3 of the first lying member L1 via a connection pipe 15, and the absorption port 7 arranged at the lid 3 of the third lying member L3 is connected to the discharge port 8 arranged at the lid 3 of the second lying member L2 via the connection pipe 15, and the absorption port 7 arranged at the lid 3 of the fourth lying member L4 is connected to the discharge port 8 arranged at the lid 3 of the third lying member L3 via the connection pipe 15.

A closing stopper 16 arranged at the lid 3 of the fourth lying member L4 is connected to the discharge port 8 arranged at the lid 3 of the lying member L4 of the terminal row, that is, the canister bottle E4 via the connection pipe 15; accordingly, the discharge port 8 arranged at the lid 3 of the lying member L4 of the terminal row, that is, the canister bottle E4 becomes closed.

As shown in FIG. 6, an end portion of the connection pipe 15 is connected to the discharge port 8 arranged at the lid 3 of the respective lying member L in a pivotally movable and airtight manner. The pivotally moving the connection pipe 15 around the discharge port 8 as a center allows another end portion of the connection pipe 15 to selectively connect with either the absorption port 7 formed at the lid 3 of a lying member L adjoined downstream (left side of FIG. 6) or the closing stopper 16 of thus lid 3.

Accordingly, as shown in FIG. 6, when a lying member Ln arranged at the terminal row is connected to a downstream arranged lying member L n+1 for newly making the lying member L n+1 to become the lying member L arranged at the terminal row, the opening rim portion of the connection pipe 15 illustrated with a full line in FIG. 6 and rotatively attached to the discharge port 8 of the lid 3 of the lying member Ln (shown in FIG. 7) is pulled out from the closing stopper 16, and then is inserted and connected to the absorption port 7 of the lid 3 of the lying member Ln+1 illustrated with a broken line in FIG. 6, and further, an opening rim portion of the connection pipe 15 rotatively attached to the discharge port 8 of the lid 3 of the lying member Ln+1 is inserted to a closing stopper 16 of the lid 3 for closure.

A valve member 15a is arranged at an opening rim portion of the connection pipe 15 and as shown in FIG. 8(a), when connecting the opening rim portion of the connection pipe 15 to the absorption port 7, the connection pipe 15 is in air-communication with the absorption port 7 in which a projecting portion 7a arranged at a surrounding of an opening portion of the absorption port 7 is pushed upward to open a rubber valve 15a1 formed at the valve member 15a and further, a letter O shaped ring arranged at an outer peripheral portion of the valve member 15a is pressingly contacting to an inner wall of an opening portion of the absorption port 7 so as to maintain an airtight state.

As shown in FIG. 8(b), when connecting the opening rim portion of the connection pipe 15 to the closing stopper 16, the connection pipe 15 is closed in a state where a letter O shaped ring arranged at an outer peripheral portion of the valve member 15a is pressingly contacting to an inner wall of an opening portion of the closing stopper 16 so as to maintain an airtight state while the rubber valve 15a 1 remains shut.

Likewise, a valve member 14a is arranged at an end portion connected to the patient hose 14 on the side of the liquid waste disposal apparatus 1, and in a state where the end portion of the patient hose 14 is connected to the absorption port 7, the patient hose 14 is in air-communication with the absorption port 7 in which a projecting portion 7a arranged at a surrounding of an opening portion of the absorption port 7 is pushed upward to open a rubber valve 14a1 formed at the valve member 14a and further, a letter O shaped ring arranged at an outer peripheral portion of the valve member 14a is pressingly contacting to an inner wall of an opening portion of the absorption port 7 so as to maintain an airtight state.

As shown in FIG. 2 and FIG. 5, a controller 17 having an adjustment handle 17a for adjusting an absorption pressure (vacuum pressure) is arranged to the stand 2; the controller 17 is connected to a primary absorption hose 18 connected to a terminal takeout port (outlet valve) or an air pump of an absorption piping of a medical gas piping installation in which an adjusted absorbing pressure of the controller 17 causes an inside of the lying member L to become negative pressure via the absorption path 13 and an absorption path 20 of the exhaust port 9.

On the other hand, as shown in FIG. 5, the absorption path 13 is in air-communication with an absorption path 19 in which the absorption path 19 is connected to a gap between the bottle M and the lying member L. Since both an absorption pressure inside the lying member L and an absorption pressure of the gap between the bottle M and the lying member L are negatively pressured with an equal absorption pressure, the air pressure inside and outside of the lying member L arranged inside the bottle M becomes equal and thus, a steady absorption could be performed while maintaining a state shown in FIG. 5 without causing the lying member L formed with a flexible sheet to expand and contract.

A stop valve 9a is arranged at the exhaust port 9 and thus at an inner side of an end portion of the lying member L; further, as shown by the canister bottles E2, E3, E4 of FIG. 12, a self-weight of the stop valve 9a allows the stop valve 9a to maintain a downward position until the float 5 floats to reach the ceiling portion and subsequently, the absorption path 20 in air-communication with the absorption path 13 from inside the lying member L could be maintained.

On the other hand, as shown by the canister bottle E1 of FIG. 12, when the liquid waste 21 is absorbed into the lying member L to elevate the float 5 until the float 5 reaches the ceiling portion of the lying member L, a ceiling edge surface 5b 1 of the float 5 makes contact to the stop valve 9a and pushes the stop valve 9a upward against the self-weight of the stop valve 9a and causes the absorption path 20 in air-communication with the absorption path 13 from inside the lying member L to become closed.

Once the stop valve 9a is pushed upward to close the absorption path 20, owing to an absorbing strength of exhaust, the stop valve 9a adheres to a cylindrical body 9b arranged above so as to maintain the closed state of the absorption path 20.

The float 5 shown in FIG. 10 and FIG. 11 is placed on the bottom portion 4a of the lying member. The float 5 is structured to have a specific gravity less than 1, and as shown in FIG. 12, the float 5 always stays afloat at liquid-gas interface of the liquid waste 21 when the liquid waste 21 flows into the lying member L.

The float 5 is supported by an inner edge portion of the annular member 5a in a manner where a solidifying agent such as a water-absorptive polymer is filled and retained by the cup portion 5b in which the cup portion 5b has a face down shape with a downward opening; and thus, the annular member 5a and the cup portion 5b according to this embodiment are formed with polypropylene having a specific gravity less than 1.

As shown in FIG. 4 through FIG. 10, an outer diameter of the annular member 5a of the float 5 is formed smaller than an inner diameter of the lying member L, a bottom portion of the cup 5b is opened in a state where the float 5 is contained inside the lying member L.

In a filling process of the water-absorptive material 6 into the cup portion 5b of the float 5, as shown in FIG. 11, after the water-absorptive material 6 has been filled into the cup portion 5b where the float 5 is in an upside down state, a fixing ring 23 is engaged to peripheral portion of the cup portion 5b in a state covered by a water permeable sheet 22 e.g. Japanese traditional paper, and further a claw portion 23a of the fixing ring 23 is engaged to step portion 5b2 formed at a peripheral edge portion of the cup portion 5b.

The liquid waste 21 absorbed into the lying member L from the absorption port 7 comes around to a bottom portion via a gap between the lying member L and the annular member 5a or a gap between the cup portion 5b and the annular member 5a; then the liquid waste 21 permeates through the water permeable sheet 22 spread and stretched at a peripheral rim portion of the cup portion 5b and contacts to the water-absorptive material 6 so that the water-absorptive material 6 would swell to tear the water permeable sheet 22 and dissolve into the liquid waste 21 contained inside the lying member L to solidify the liquid waste 21 into a gel.

Hereinafter an operating procedure and an operation of the liquid waste disposal apparatus 1 will be specifically described. The lying member L is preserved and transported in a state where the holder 10 remains attached by a method such as sealing the lying member L with a vinyl-wrapping container. In thus situation, the catch 10a arranged at the holder 10 could be laid down to both sides of the lid 3, and the lying member L could be preserved and transported in a relatively compact manner since the lying member L itself is flexible.

At a time for operation, the lying member L is prepared in correspondence with the number of the bottle M arranged in a straight line at the stand 2, and then, the adjustment handle 17a is turned in a counter clockwise direction shown in FIG. 2 so as to turn the controller 17 off, and then an adapter 18a of the primary absorption hose 18 is connected to a terminal takeout port or an air pump of a medical gas piping installation (not shown).

Next, the canister bottle 12 of the stand 2 is opened to insert the lying member L into all of the bottles M, and then, the connection pipe 15 rotatively attached to the discharge port 8 formed at the lid 3 of the ceiling portion of the respective lying members L is inserted and connected to the absorption port 7 formed at the lid 3 of the ceiling portion of the lying member L adjoined to the left side in FIG. 4.

The end portion on the side of the valve member 14a of the patient hose 14 is inserted and connected to the absorption port 7 formed at the lid 3 of the ceiling portion of the lying member L1 of the first canister bottle E1 and further, in means for closure, the closing stopper 16 formed at the lid 3 of the lying member L4 is connected to the connection pipe 15 in which the connection pipe 15 is connected to the discharge port 8 formed at the lid 3 of the lying member L4 of the fourth canister bottle E4 serving as the terminal canister bottle.

Next, the canister head 12 is closed and locked to the stand 2. Before the beginning of absorption, the float 5 is arranged at the bottom portion 4 of the lying member L as shown in FIG. 4 owing to the weight of the float 5 itself.

Then, the adjustment handle 17a of the controller 17 is turned clockwise as shown in FIG. 2 so as to turn the controller 17 for adjusting to a prescribed absorption pressure. In thus case, the negative pressure of the primary absorption hose 18 causes the inside of the lying member L to become negative pressure via the absorption path 13 formed at the respective canister heads 12 and the absorption path 20 of the exhaust port 9 formed at the lid 3 of the ceiling portion of the respective lying members L; further, the gaps between the respective bottles M and the respective lying members L are also caused to become negative pressure via the absorption path 19 in air-communication with the gaps between the respective bottles M and the respective lying members L.

In this process, the presence of absorption pressure inside the lying member L is to be confirmed by closing a tip of the patient hose 14 and whether or not the lying member L inflates along the bottle M is also to be confirmed.

When an absorption of the liquid waste 21 is started after a tip of the patient hose 14 is applied to such as an affected area of the patient, as shown in FIG. 12, the liquid waste 21 from the patient hose 14 is guided into the lying member L via the absorption port 7 formed at the lid 3 of the lying member L1 of the first canister bottle E1.

The liquid waste 21 absorbed into the lying member L1 reaches below the float 5 via the gap between the lying member L1 and the annular member 5a of the float 5 or via the gap between the cup portion 5b and the annular member 5a of the float 5.

Since the float 5 has a specific gravity less than 1 the float 5, the float maintains a position at the level of the liquid waste 21 and stays afloat at liquid-gas interface; thus, the liquid waste 21 permeates through the water permeable sheet 22 spread and stretched at a bottom surface of a peripheral rim portion of the cup portion 5b of the float 5 and contacts to the water-absorptive material 6 so that the water-absorptive material 6 would swell to tear the water permeable sheet 22 and spread among the liquid waste 21 and solidify the liquid waste 21 into a gel.

Even after the progress of the absorption of the liquid waste 21, the water-absorptive material 6 could effectively spread among the liquid waste 21 absorbed afterwards and solidify thus liquid waste 21 into a gel since the float 5 constantly stays afloat at the liquid-gas interface.

Further, since the float 5 constantly stays afloat at the liquid-gas interface, the amount of the absorbed liquid waste 21 could easily be visually recognized so that the float 5 could function as a level gauge as well. Therefore, it is suitable for such as the annular member 5a or the cup portion 5b of the float 5 to be formed with a material having a color distinguishable with the color of the liquid waste 21 or a distinguishing color such as a florescent color.

As shown in FIG. 12, as the absorption process of the liquid waste 21 progresses, the float 5 elevates to the ceiling portion of the lying member L and then, the ceiling edge surface 5b1 serving as the upward-pushing portion of the cup portion 5b of the float 5 pushes the stop valve 9a upward against the weight of the stop valve 9a so that the absorption path 20 becomes closed and the absorption pressure from the exhaust port 9 would cease, as a manner as first canister bottle E1 of FIG. 12.

With the cease of the absorption pressure inside the lying member L1, an absorption pressure of the L2 adjoined at the left side of the lying member L1 in FIG. 12 affects the inside of the lying member L1 via the absorption path 13 of the stand 2, the absorption path 20 of the exhaust port 9 of the lying member L2, the absorption port 7 of the lying member L2, the connection pipe 15, the discharge port 8 of the lying member L1; the not-yet gelled liquid waste 21 absorbed above the float 5 inside the lying member L1 is absorbed into the lying member L2 via the discharge port 8 of the lying member L1, the connection pipe 15 and the absorption port of the lying member L2.

In the same manner as the foregoing lying member L1, the float 5 elevates and stays afloat at the level of the liquid waste 21 in correspondence with the rise in the level of the liquid waste 21 contained inside the lying member L2, and when the float 5 reaches the ceiling portion of the lying member L2, the ceiling edge surface 5b1 of the float 5 pushes the stop valve 9a upward to close the absorption path 20 and cease the absorption pressure of the lying member L2.

Likewise, an absorption pressure of the lying member L3 adjoined to the lying member L2 absorbs the absorbed liquid waste 21 contained above the float 5 of the lying member L2 into the lying member L3 via the discharge port 8 of the lying member L2, the connection pipe 15 and the absorption port of the lying member L3.

In the same manner as the foregoing lying members L1, L2, the float 5 elevates and stays afloat at the level of the liquid waste 21 in correspondence with the rise in the level of the liquid waste 21 contained inside the lying member L3, and when the float 5 reaches the ceiling portion of the lying member L2, the ceiling edge surface 5b1 of the float 5 pushes the stop valve 9a upward to close the absorption path 20 and cease the absorption pressure of the lying member L3.

Likewise, an absorption pressure of the lying member L4 adjoined to the lying member L3 absorbs the absorbed liquid waste 21 contained above the float 5 of the lying member L3 into the lying member L4 via the discharge port 8 of the lying member L3, the connection pipe 15 and the absorption port of the lying member L4.

In the same manner as the foregoing lying members L1, L2, L3, the float 5 elevates and stays afloat at the level of the liquid waste 21 in correspondence with the rise in the level of the liquid waste 21 contained inside the lying member L4, and when the float 5 reaches the ceiling portion of the lying member L4, the ceiling edge surface 5b1 of the float 5 pushes the stop valve 9a upward to close the absorption path 20 and cease the absorption pressure of the lying member L4.

Therefore, since each float 5 upwardly pushes and activates the stop valve 9a, the absorption of the liquid waste 21 is automatically ceased before all of the lying members L become full with liquid waste 21; accordingly, the air-pump or the like would not malfunction due to an excessive absorption into the respective lying members L.

After the use of the liquid waste disposal apparatus, the lying member L is taken out from the bottle M by opening the canister head 12 of the stand 2, and then, an end portion of the connection pipe 15 is inserted and connected to the absorption port 7 arranged at the lid 3 wherein another end-portion of the connection pipe is rotatively connected to the discharge port 8 of the lid 3 of the respective lying members L, and then, as shown in FIG. 5, FIG. 6, FIG. 8(b) and FIG. 9(a), a cap 24 prearranged to the lid 3 covers the exhaust port 9 arranged at the lid 3 of the respective lying members L for hermetically sealing the lying members L, and subsequently, pulling out the lying member L with the catch 10a of the holder 10 enables easy detachment from the bottle M so that the lying member L could solely be disposed by incineration and the like.

Further, the lying member could be solely stood upright owing to a function of the bottom portion 4 of the lying member L in a state where the liquid waste 21 inside the lying member L is gelled by the water-absorptive material 6.

The liquid waste 21 remaining inside the connection pipe 15 or the patient hose 14 would not drip down during a detachment of the patient hose 14 or the connection pipe 15 from the absorption port 7 owing to a function of the rubber valves 14a1, 15a1 of the valve members 14a, 15a of the connection pipe 15 or the patient hose 14.

Although this embodiment is described showing 4 canister bottles E1, E2, E3, and E4 arranged in a straight line in which the discharge port 8 of the lid 3 of each lying member L is connected to the absorption port 7 of the lid 3 of each adjoining lying member L, this invention could be structured having n canister bottles (n being equal to or more than 2) arranged in a straight line in which the discharge port 8 of the lid 3 of the first lying member L1 of the first canister bottle E1 is connected to the absorption port 7 of the lid 3 of the second lying member L2 of the second canister bottle E2, and the discharge port 8 of the lid 3 of the second lying member L2 of the second canister bottle E2 is connected to the absorption port 7 of the lid 3 of the third lying member L3 of the third canister bottle E3, and . . . the discharge port 8 of the lid 3 of the n−1 lying member of n−1 canister bottle is connected to the absorption port 7 of the lid 3 of the n lying member Ln of the n canister bottle En.

Thus structured, the liquid waste 21 could be absorbed and contained consecutively into the lying member L of the serially connected multiple canister bottles E by connecting the discharge port 8 of the lid 3 of the lying member L of one canister bottle E to the absorption port 7 of the lid 3 of the lying member L of another canister bottle E via the connection pipe 15 and forming a serial connection while closing the discharge port 8 of the canister bottle E4 arranged at the terminal row to allow exhaustion from the exhaust port 9 of each canister bottle E for internally creating negative pressure.

The kind of canister bottle could be reduced to allow the reduction of production cost and product management cost since the kind of lying member L of canister bottle E used for the lying member L4 of canister bottle E4 arranged at the terminal row is unified with that of the other lying members L1, L2, L3 of canister bottles E1, E2, E3.

All of the canister bottles E could be viewed from a single direction by serially connecting the canister bottles E in an order starting from the first canister bottle E1 to the n (n being equal to or more than 3) canister bottle En and forming a straight line; the user of the disposal apparatus 1 could easily confirm the remaining containment capacity of the disposal apparatus 1 since the liquid waste 21 is contained in an order starting from the first canister bottle E1 to the n canister bottle En.

By providing the canister bottle E comprised of the bottle M serving as the outer container having inside the lying member L serving as the internal bag containing the water absorptive material 6 serving as the solidifying agent, the liquid waste 21 could be solidified inside the lying member L so that the lying member L could be solely and sanitarily disposed.

By providing the float 5 inside the lying member L of the canister bottle E in which the float 5 retains the water-absorptive material 6 serving as the solidifying agent and has a specific gravity less than 1, the liquid level of the liquid waste 21 could be easily confirmed from outside by checking the position of the float 5 since the float 5 would always remain afloat at a gas-liquid interface, and the user could also confirm with certainty the used amount of the canister bottle E as well as the remaining containment capacity.

Next, referring to FIGS. 13 to FIG. 16, a structure of the multiple continuous type liquid waste disposal apparatus regarding the second embodiment will hereinafter be explained. It should be noted that constitutions similar to those explained in the first embodiment will be assigned with the same reference numerals, while omitting the explanations thereof.

Figure 13:
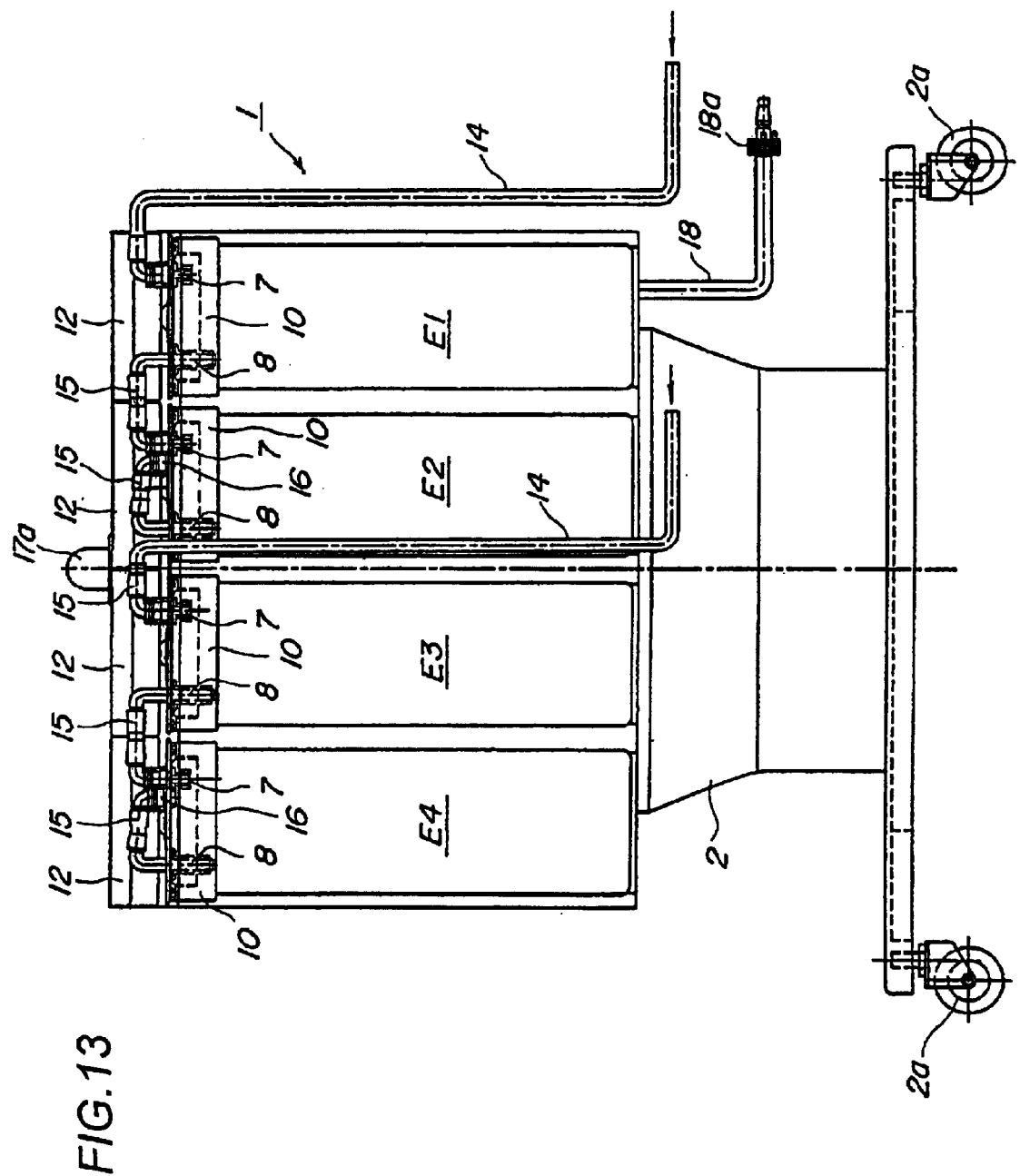
FIG. 13 is an outer front view of a second embodiment of the multiple continuous type liquid waste disposal apparatus regarding this invention showing an example where canister bottles are separated into two groups and a patient hose is connected to an absorption port of the respective canister bottle groups.
Figure 14:
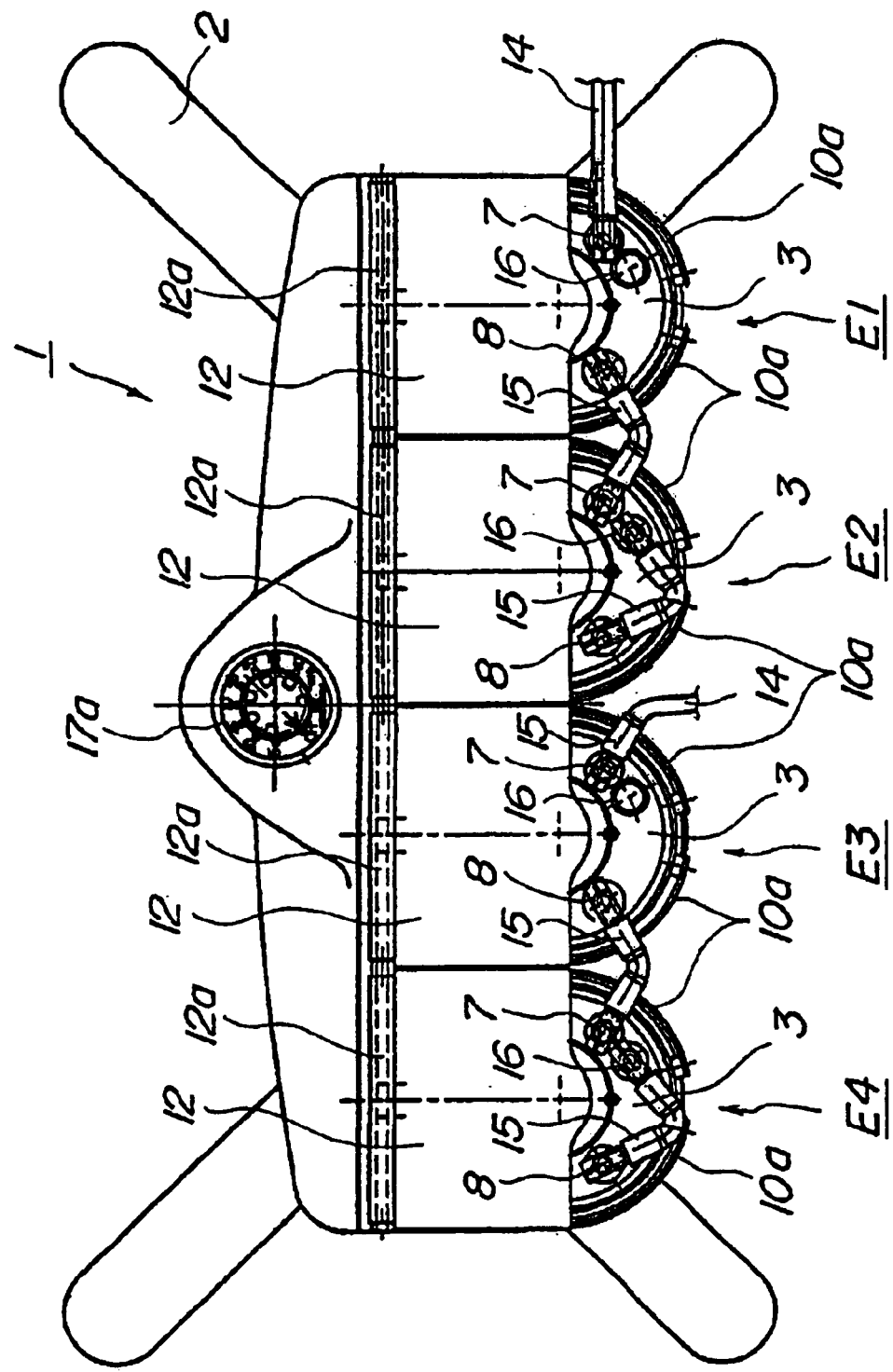
FIG. 14 is an outer plane view of a second embodiment of the multiple continuous type liquid waste disposal apparatus regarding this invention showing an example where the canister bottles are separated into two groups and a patient hose is connected to an absorption port of the respective canister bottle groups.

FIG. 13 is an outer front view of the second embodiment of the multiple continuous type liquid waste disposal apparatus regarding this invention showing an example where canister bottles are separated into two groups and a patient hose is connected to an absorption port of the respective canister bottle groups; and FIG. 14 is an outer plane view of the second embodiment of the multiple continuous type liquid waste disposal apparatus regarding this invention showing an example where the canister bottles are separated into two groups and a patient hose is connected to an absorption port of the respective canister bottle groups.

Figure 15:
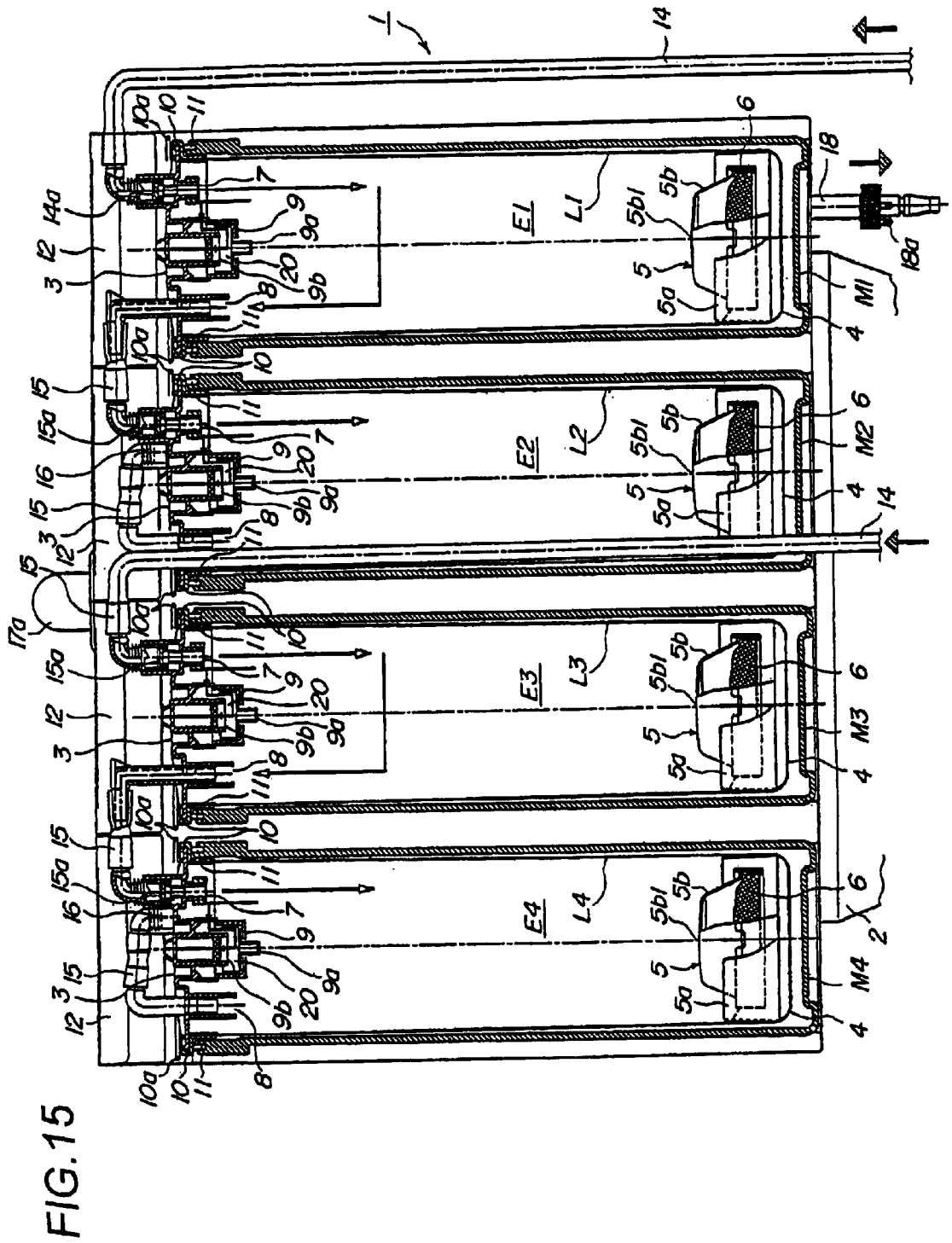
FIG. 15 is front vertical cross-section view of a second embodiment of the multiple continuous type liquid waste disposal apparatus regarding this invention explaining an example of an absorption path wherein the canister bottles are separated into two groups and a patient hose is connected to an absorption port of the respective canister bottle groups.
Figure 16:
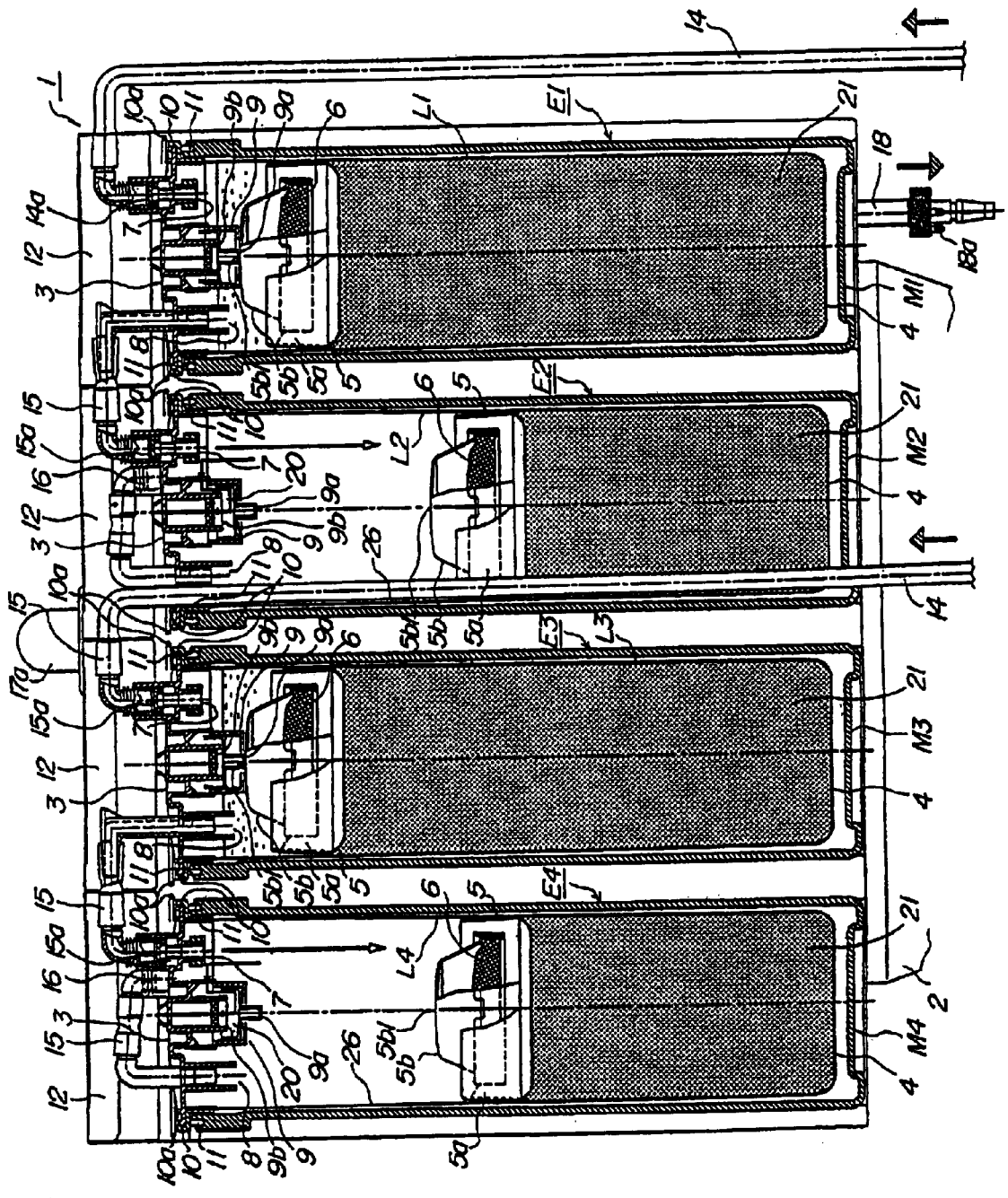
FIG. 16 is a view of a second embodiment of the multiple continuous type liquid waste disposal apparatus regarding this invention showing a state where a liquid waste is absorbed and contained wherein the canister bottles are separated into two groups and a patient hose is connected to an absorption port of the respective canister bottle groups.

FIG. 15 is front vertical cross-section view of the second embodiment of the multiple continuous type liquid waste disposal apparatus regarding this invention explaining an example of an absorption path wherein the canister bottles are separated into two groups and a patient hose is connected to an absorption port of the respective canister bottle groups; and FIG. 16 is a view of the second embodiment of the multiple continuous type liquid waste disposal apparatus regarding this invention showing a state where a liquid waste is absorbed and contained wherein the canister bottles are separated into two groups and a patient hose is connected to an absorption port of the respective canister bottle groups.

As shown in FIG. 13 through FIG. 16, in respect of this embodiment, the first canister bottle E1, the second canister bottle E2, the third canister bottle E3 and the fourth canister bottle E4 are arranged to form a straight line in an order starting from the first canister bottle E1, the second canister bottle E2, the third canister bottle E3 and to the fourth canister bottle E4; a group of canister bottles E comprised of the first canister bottle E1, the second canister bottle E2, the third canister bottle E3 and the fourth canister bottle E4 are separated into two groups which are a group comprising the first canister bottle E1 and the second canister bottle E2, and a group comprising the third canister bottle E3 and the fourth canister bottle E4.

Separate patient hoses 14 are respectively connected to the absorption port 7 arranged at the lid 3 of the first and third lying member L1, L3 of the first and third canister bottle E1, E3 in which both canister bottles serve as the primary canister bottle for each of the separated canister bottle group E; a tip of each patient hose 14 is applied upon a portion such as an affected portion of a patient so as to absorb the liquid waste 21 such as dispensable blood, other body fluids, secretion, pus, or physiological sodium chloride solution used for cleansing affected areas produced during operation and treatment.

The discharge port 8 arranged at the lid 3 of the first lying member L1 is connected to the absorption port 7 arranged at the lid 3 of the second lying member L2 via the connection pipe 15, and the discharge port 8 arranged at the lid 3 of the third lying member L2 is connected to the absorption port 7 arranged at the lid 3 of the fourth lying member L4 via the connection pipe 15; each group of the plural canister bottles E are serially connected in order to form a straight line.

Via the connection pipe 15, each closing stopper 16 arranged at the lid 3 of the second and fourth lying member L2, L4 is respectively connected to the discharge port 8 arranged at the lid 3 of the lying members L2, L4 of the canister bottles E2, E4 in which both canister bottles serve as the terminal canister bottle for each of the separated canister bottle groups; accordingly, each discharge port 8 arranged at the lid 3 of the lying members L2, L4 of the canister bottles E2, E4 serving as the terminal canister bottle for each of the separated canister bottle groups becomes closed.

Consequently, in correspondence with the number of patient hoses 14 required for use and the absorption amount of liquid waste 21 absorbed from each patient hose, a desired number of canister bottles E could be serially connected with use of the connection pipe 15, and the group of canister bottles E could be separated in correspondence with the number of patient hoses 14 required for use.

In means to alter the number of separated canister bottles, the opening rim portion of the connection pipe 15 rotatively attached to the discharge port of the lid 3 of the terminal lying member L of a newly separated canister bottle group is pulled out from the absorption port 7 of an upstream adjoined lying member L, and then is inserted to the closing stopper 16 of the lid 3 of the terminal lying member L for closure, and further, a patient hose 14 is inserted and connected to the absorption port 7 of the lid 3 of the primary lying member L of the newly separated canister bottle group.

Likewise, a valve member 14a is arranged at an end portion connected to the patient hose 14 on the side of the absorption port 7, and in a state where the end portion of the patient hose 14 is connected to the absorption port 7, the patient hose 14 is in air-communication with the absorption port 7 in which a projecting portion 7a arranged at a surrounding of an opening portion of the absorption port 7 is pushed upward to open a rubber valve 14a1 formed at the valve member 14a and further, a letter O shaped ring arranged at an outer peripheral portion of the valve member 14a is pressingly contacting to an inner wall of an opening portion of the absorption port 7 so as to maintain an airtight state.

A stop valve 9a is arranged at the exhaust port 9 and thus at an inner side of an end portion of the lying member L; further, as shown by the canister bottles E2, E4 of FIG. 16, a self-weight of the stop valve 9a allows the stop valve 9a to maintain a downward position until the float 5 floats to reach the ceiling portion and subsequently, the absorption path 20 in air-communication with the absorption path 13 from inside the lying member L could be maintained.

On the other hand, as shown by the canister bottles E1, E3 of FIG. 16, when the liquid waste 21 is absorbed into the lying member L to elevate the float 5 until the float 5 reaches the ceiling portion of the lying member L, a ceiling edge surface 5b1 of the float 5 makes contact to the stop valve 9a and pushes the stop valve 9a upward against the self-weight of the stop valve 9a and causes the absorption path 20 in air-communication with the absorption path 13 from inside the lying member L to become closed.

In the same manner as the first embodiment, the canister bottle 12 of the stand 2 is opened to insert the lying member L into all of the bottles M, and then, in the number according to necessity, the connection pipe 15 rotatively attached to the discharge port 8 formed at the lid 3 of the ceiling portion of the respective lying members L is inserted and connected to the absorption port 7 formed at the lid 3 of the ceiling portion of the lying member L adjoined to the left side in FIG. 15.

This embodiment shows an example where the connection pipe 15 rotatively attached to the discharge port 8 formed at the lid 3 of the first lying member L1 is inserted and connected to the absorption port 7 formed at the lid 3 of the second lying member L2, and the connection pipe 15 rotatively attached to the discharge port 8 formed at the lid 3 of the third lying member L3 is inserted and connected to the absorption port 7 formed at the lid 3 of the fourth lying member L4.

An end arranged at the side of the valve 14a of each patient hose 14 is inserted and connected to each absorption port 7 formed at the lid 3 arranged at the ceiling edge portion of the lying members L1, L3 of the first and third canister bottles E1, E3 serving as the primary canister bottle for each of the separated canister bottle groups.

Each closing stopper 16 formed at the lid 3 of the lying members L2, L4 is closed by connecting to each connection pipe 15 connected to the discharge port 8 formed at the lid 3 arranged at the ceiling edge of the lying members L2, L4 of the second and fourth canister bottles E2, E4 serving as the terminal canister bottle for each of the separated canister bottle groups.

In this process, the presence of absorption pressure inside the lying member L is to be confirmed by closing a tip of each patient hose 14 and whether or not the lying member L inflates along the bottle M is also to be confirmed.

As shown in FIG. 16, after a tip of each patient hose 14 is applied to an affected area or the like of a same patient or a different patient, and after the absorption of the liquid waste 21 is started, the liquid waste 21 from each patient hose 14 is guided into the lying members L1, L3 via the absorption port 7 formed at the lid 3 of the lying members L1, L3 of the first and third canister bottles E1, E3.

The liquid waste 21 absorbed into the lying member L1, L3 reaches below the float 5 via the gap between the lying members L1, L3 and the respective annular member 5a of the float 5 or via the gap between the cup portion 5b and the annular member 5a of the float 5.

Since each float 5 has a specific gravity less than 1 the float 5, the float maintains a position at the level of the liquid waste 21 and stays afloat at liquid-gas interface; thus, the liquid waste 21 permeates through the water permeable sheet 22 spread and stretched at a bottom surface of a peripheral rim portion of the cup portion 5b of the float 5 and contacts to the water-absorptive material 6 so that the water-absorptive material 6 would swell to tear the water permeable sheet 22 and spread among the liquid waste 21 and solidify the liquid waste 21 into a gel.

As shown in FIG. 16, as the absorption process of the liquid waste 21 progresses, each float 5 elevates to the ceiling portion of the lying member L and then, the ceiling edge surface 5b1 of the cup portion 5b of the float 5 pushes the stop valve 9a upward against the weight of the stop valve 9a so that the absorption path 20 becomes closed, and as shown in a manner as the first and third canister bottle E1, E3 in FIG. 16, the absorption pressure from the exhaust port 9 ceases.

With the cease of the absorption pressure inside the respective lying members L1, L3, an absorption pressure of each lying member L2, L4 adjoined at the left side of the respective lying members L1, L3 in FIG. 16 affects the inside of the lying members L1, L3 via the absorption path 13 of the stand 2, the absorption path 20 of the exhaust port 9 of the lying members L2, L4, the absorption port 7 of the lying members L2, L4, the connection pipe 15 and the discharge port 8 of the lying members L1, L3; the not-yet gelled liquid waste 21 absorbed above the float 5 inside the lying member L1, L3 is respectively absorbed into the lying members L2, L4 via the discharge port 8 of the lying member L1, L3, the connection pipe 15 and the absorption port of the lying member L2, L4.

In the same manner as the foregoing lying members L1, L3, the float 5 elevates and stays afloat at the level of the liquid waste 21 in correspondence with the rise in the level of the liquid waste 21 contained inside the lying member L2, L4 and when each float 5 reaches the ceiling portion of the lying member L2, L4, the ceiling edge surface 5b1 of the float 5 pushes the stop valve 9a upward to close the absorption path 20 and cease the absorption pressure of the respective lying members L2, L4.

Although this embodiment is described showing a group of 4 canister bottles E1, E2, E3, E4 arranged in a straight line and separated into two groups (one group comprising the first and second canister bottle E1, E2, and the other group comprising the third and fourth canister bottle E3, E4), the group of plural canister bottles E could also be separated into other number of groups of plural canister bottles having a suitable amount of canister bottles arranged in a straight line.

Further, the patient hose 14 connected to the canister bottle E could be of a singular patient hose.

Thus structured, the plural patient hoses 14 for each of the separated canister bottle groups E to be used separately and enables the liquid waste 21 to be absorbed and contained consecutively into the serially connected multiple canister bottles E by providing the structure wherein: each of the canister bottles E has an exhaust port 9 for internally creating negative pressure; the canister bottles E are separated into at least two groups in which the discharge port 8 of one canister bottle E is connected to the absorption port 7 of the other canister bottle E in a serially connected manner; each of the separated canister bottle groups has a terminal canister bottle E with a closed discharge port 8; and each of the separated canister bottle groups has a primary canister bottle E with a patient hose 14 connected to the absorption port 7.

The kind of canister bottle could be reduced to allow the reduction of production cost and product management cost since the kind of canister bottle E used for the canister bottle E arranged at the terminal row of the respective separated canister bottle group is unified with that of the other canister bottles E.

Further, all of the canister bottles E could be viewed from a single direction by serially connecting the plural canister bottles E regarding each group of canister bottles in an orderly manner so as to form a straight line; this invention also allows the user of the disposal apparatus to easily confirm the remaining containment capacity of the disposal apparatus since the liquid waste 21 is contained in the order according to the arrangement of the canister bottles E regarding each group of canister bottles. Although the annular member 5a, the cup portion 5b and the fixing ring 23 of this embodiment is formed from a polypropylene material having a specific gravity less than 1, as long as the specific gravity of the float 5 is less than 1, the material of thus portions is not to be limited to polypropylene.

Although the shape of the float 5 formed as a cup in a face down manner, the shape of the float 5 of this invention is not to be limited and any shape is acceptable as long as the bottom portion of the float 5 is opened (e.g. a cylinder or a polygon having a same top surface as the ceiling-edge surface or a shape having a ring-like float at a center with an arm for retaining the water-absorptive material 6). The inner portion of the cup portion 5b serving as a retaining container for retaining the water-absorptive material 6 is desired to have a ventilation hole, a slit or the like for preventing an accumulation of air.

As examples regarding the retaining means for retaining the water-absorptive material 6 inside the cup portion 5b, the water permeable sheet 22 (e.g. traditional Japanese paper) are given above, however, other means for retaining the water-absorptive material 6 could be used such as a means by solidifying the water-absorptive material 6 with a water-dissolvable filling material, a means by retaining with a water-decomposable non-fabric paper or a non-fabric cloth.

Although the foregoing embodiments are examples describing a float 5 contained inside the flexible lying member L, the float could be contained inside a container without a flexible structure.

The foregoing description of a preferred embodiment of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined by the claims set forth below.

What is claimed is:

1. A multiple continuous type liquid waste disposal apparatus comprising:

plural connected canister bottles for serving to contain liquid waste absorbed, each of the canister bottles having an absorption port for absorbing liquid waste, each of the canister bottles having a discharge port for discharging liquid waste, each of the canister bottles having an exhaust port for creating negative pressure inside of the canister bottle, a stand for holding the plural connected canister bottles in a straight line by being serially connected in order, said stand having a canister head capable of pivotal movement for connecting an absorption path disposed thereof to the exhaust port of the canister bottles, wherein the discharge port of one canister bottle being connected by a connection pipe to the absorption port of another canister bottle in a serially connected manner, and the discharge port of the last canister bottle arranged at a terminal row being closed.

2. The multiple continuous type liquid waste disposal apparatus according to claim 1, wherein the canister bottle comprises an outer container and an internal bag contained inside the outer container with a solidifying agent contained inside of the internal bag.

3. The multiple continuous type liquid waste disposal apparatus according to claim 2, wherein the internal bag of the canister bottle contains a float retaining the solidifying agent.

4. The multiple continuous type liquid waste disposal apparatus according to claim 3, wherein the exhaust port comprises a stop valve for stopping absorption of liquid waste when the float reaches and closes said stop valve.

5. A multiple continuous type liquid waste disposal apparatus comprising:

plural connected transparent canister bottles for serving to contain the liquid waste absorbed, each canister bottle comprising a transparent outer bottle and a transparent inner bag;

a float disposed in said canister bottle and capable of moving from a bottom to a top of the canister bottle, for indicating a level of the liquid waste, said float retaining solidifying agent therein for solidifying the liquid waste contained in said canister bottle;

each of the transparent canister bottles having an absorption port for receiving liquid waste to be absorbed, a discharge port for discharging liquid waste, and an exhaust port for creating and maintaining negative pressure inside of the canister bottles;

a stand for holding plural connected transparent canister bottles in a straight line by being serially connected in order;

wherein the discharge port of one transparent canister bottle is connected to the absorption port of another transparent canister bottle in a serially connected manner disposed in a line, the discharge port of the last transparent canister bottle arranged at a terminal row is closed, and the float acts as a level gauge, allowing a user to determine the quantity of liquid waste contained in the transparent canister bottle.

6. The multiple continuous type liquid waste disposal apparatus according to claim 5, wherein the stand comprises a canister head capable of pivotal movement for connecting an absorption path disposed thereof to exhaust ports of canister bottles.

7. The multiple continuous type liquid waste disposal apparatus of claim 5, said float therein further comprising a water-absorptive retaining container, and water-absorptive material contained within said water-absorptive retaining container, wherein when said water-absorptive material absorbs a maximum quantity of liquid, said water-absorptive retaining container is ruptured, allowing the solidifying agent to be released from the float into the liquid waste.

* * * * *